US010172909B2

(12) United States Patent
White et al.

(10) Patent No.: US 10,172,909 B2
(45) Date of Patent: Jan. 8, 2019

(54) NEUROPEPTIDE ANALOGS, COMPOSITIONS, AND METHODS FOR TREATING PAIN

(71) Applicants: NeuroAdjuvants, Inc., Salt Lake City, UT (US); The University of Utah Research Foundation, Salt Lake City, UT (US)

(72) Inventors: H. Steve White, Salt Lake City, UT (US); Brian Donald Klein, Salt Lake City, UT (US); Cameron Spencer Metcalf, Sandy, UT (US); Daniel Ryan McDougle, Urbana, IL (US); Erika Adkins Scholl, Sandy, UT (US); Misty Danielle Smith, West Valley City, UT (US); Grzegorz Bulaj, Salt Lake City, UT (US); Liuyin Zhang, Salt Lake City, UT (US)

(73) Assignee: THE UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 15/183,389

(22) Filed: Jun. 15, 2016

(65) Prior Publication Data

US 2017/0020951 A1    Jan. 26, 2017

Related U.S. Application Data

(62) Division of application No. 13/994,675, filed as application No. PCT/US2011/064977 on Dec. 14, 2011, now abandoned.

(60) Provisional application No. 61/423,530, filed on Dec. 15, 2010.

(51) Int. Cl.
| | |
|---|---|
| *A61K 38/10* | (2006.01) |
| *A61K 38/22* | (2006.01) |
| *A61K 38/31* | (2006.01) |
| *C07K 7/08* | (2006.01) |
| *C07K 14/575* | (2006.01) |
| *C07K 14/655* | (2006.01) |
| *A61K 47/48* | (2006.01) |

(52) U.S. Cl.
CPC .......... *A61K 38/10* (2013.01); *A61K 38/2271* (2013.01); *A61K 38/31* (2013.01); *A61K 47/48215* (2013.01); *C07K 7/083* (2013.01); *C07K 14/57545* (2013.01); *C07K 14/655* (2013.01)

(58) Field of Classification Search
None
See application file for complete search history.

(56) References Cited

U.S. PATENT DOCUMENTS

| | | | |
|---|---|---|---|
| 3,610,795 | A | 10/1971 | Antoine |
| 4,704,692 | A | 11/1987 | Ladner |
| 4,868,116 | A | 9/1989 | Morgan et al. |
| 4,897,355 | A | 1/1990 | Eppstein et al. |
| 4,980,286 | A | 12/1990 | Morgan et al. |
| 5,670,477 | A | 9/1997 | Poduslo et al. |
| 5,965,788 | A | 10/1999 | Houdebine et al. |
| 6,261,834 | B1 | 7/2001 | Srivastava |
| 7,786,133 | B2 | 8/2010 | Bentley et al. |
| 8,435,940 | B2 | 5/2013 | Bulaj et al. |
| 8,933,020 | B2 | 1/2015 | Bulaj et al. |
| 2002/0013266 | A1 | 1/2002 | Bentley et al. |
| 2005/0186174 | A1 | 8/2005 | Bossard |
| 2009/0281031 | A1 | 11/2009 | Bulaj et al. |
| 2013/0324467 | A1 | 12/2013 | White et al. |
| 2015/0203554 | A1 | 7/2015 | Bulaj et al. |

FOREIGN PATENT DOCUMENTS

| | | |
|---|---|---|
| EP | 0 514 361 A1 | 11/1992 |
| EP | 0 527 063 A1 | 2/1993 |
| EP | 1 217 071 A1 | 6/2002 |
| EP | 2 651 429 | 10/2013 |
| WO | 1989/07136 A2 | 8/1989 |
| WO | 1990/02806 A1 | 3/1990 |
| WO | 2001/07473 A1 | 2/2001 |
| WO | 2002/098446 A1 | 12/2002 |
| WO | 2007/081792 A2 | 7/2007 |
| WO | 2012/082942 | 6/2012 |

OTHER PUBLICATIONS

European Communication for corresponding European Application No. 14 200 660.0-1401, dated Nov. 10, 2016, 5 pages.
Abrahmsén, et al., "Engineering Subtilisin and Its Substrates for Efficient Ligation of Peptide Bonds in Aqueous Solution," Biochemistry, vol. 30, pp. 4151-4159, (1991).
Anthony-Cahill, et al., "Site-specific mutagenesis with unnatural amino acids," TIBS, vol. 14, No. 10, pp. 400-403, (Oct. 1989).
Acsadi et al., "Human dystrophin expression in mdx mice after intramuscular injection of DNA constructs," Nature 352:815-818, Aug. 29, 1991.
Australian Examination Report for corresponding Australian Application No. 2011343822, dated Jun. 16, 2016, 4 pages.
Bagshawe et al., "A cytotoxic agent can be generated selectively at cancer sites," Br. J. Cancer 58:700-703, 1988.
Bagshawe, "The First Bagshawe Lecture: Towards generating cytotoxic agents at cancer sites," Br. J. Cancer 60:275-281, 1989.
Baggiolini, et al., "Interleukin-8, a chemotactic and inflammatory cytokine," Federation of European Biochemical Societies, vol. 307, No. 1, pp. 97-101, (Jul. 1992).

(Continued)

*Primary Examiner* — James H Alstrum-Acevedo
*Assistant Examiner* — Tara L Martinez
(74) *Attorney, Agent, or Firm* — Ballard Spahr LLP

(57) ABSTRACT

Neuropeptide analogs and compositions including neuropeptide analogs are described herein. Also provided are methods of producing and using the neuropeptide analogs and compositions including one or more neuropeptide analogs.

2 Claims, 10 Drawing Sheets

Specification includes a Sequence Listing.

(56) References Cited

OTHER PUBLICATIONS

Banerji et al., "A Lymphocyte-Specific Cellular Enhancer Is Located Downstream of the Joining Region in Immunolglobulin Heavy Chain Genes," Cell 33:729-740, Jul. 1983.
Banks et al., "Permeability of the Blood-Brain Barrier to Peptides: An Approach to the Development of Therapeutically Useful Analogs," Peptides 13(6):1289-1294, Nov. 1992.
Banks et al., "Peptides and the Blood-Brain Barrier: Lipophilicity as a Predictor of Permeability," Brain Research Bulletin 15:287-292, 1985.
Battelli et al., "T lymphocyte killing by a xanthine-oxidase-containing immunotoxin," Cancer Immunol. Immunother. 35:421-425, 1992.
Benner, S.A., "Expanding the genetic lexicon: incorporating nonstandard amino acids into proteins by ribosome-based synthesis," TIBTECH, vol. 12, pp. 158-163, (May 1994).
Berkner et al., "Abundant expression of polyomavirus middle T antigen and dihydrofolate reductase in an adenovirus recombinant," Journal of Virology 61(4):1213-1220, Apr. 1987.
Bickel et al., "Delivery of peptides and proteins through the blood-brain barrier," Advanced Drug Delivery Reviews 10(2-3):205-245, May 1993.
Bout et al., "Lung Gene Therapy: In Vivo Adenovirus-Mediated Gene Transfer to Rhesus Monkey Airway Epithelium," Human Gene Therapy 5:3-10, 1994.
Brigham et al., "Expression of a Prokaryotic Gene in Cultured Lung Endothelial Cells after Lipofection with a Plasmid Vector," Am. J. Respir. Cell. Mol. Biol. 1:95-100, 1989.
Brown et al., "Molecular and Cellular Mechanisms of Receptor-Mediated Endocytosis," DNA and Cell Biology 10(6):399-409, 1991.
Brown et al., "Penetration of Host Cell Membranes by Adenovirus 2," Journal of Virology 12(2):386-396, Aug. 1973.
Bulaj, et al., "Design, Synthesis, and Characterization of High-Affinity, Systemically-Active Galanin Analogues with Potent Anticonvulsant Activities," J. Med. Chem., vol. 51, pp. 8038-8047, (2008).
Caillaud et al., "Adenoviral Vector as a Gene Delivery System into Cultured Rat Neuronal and Glial Cells," European Journal of Neuroscience 5:1287-1291, 1993.
Chapman et al., "The Effects of Sandostatin and Somatostatin on Nociceptive Transmission in the Dorsal Horn of the Rat Spinal Cord," Neuropeptides 23:147-152, 1992.
Chaplan, et al., "Quantitative assessment of tactile allodynia in the rat paw," Journal of Neuroscience Methods, vol. 53, pp. 55-63, (1994).
Chardonnet et al., "Early Events in the Interaction of Adenoviruses with HeLa Cells: I. Penetration of Type 5 and Intracellular Release of the DNA Genome," Virology 40:462-477, 1970.
Chen et al., "Drug Delivery Across the Blood-Brain Barrier," Current Drug Delivery 1:361-376, 2004.
Clark-Lewis, et al., "Structural Requirements for Interleukin-8 Function Identified by Design of Analogs and CXC Chemokine Hybrids," Journal of Biological Chemistry, vol. 269, No. 23, pp. 16075-16081, (Jun. 10, 1994).
Clark-Lewis, et al., "Chemical Synthesis, Purification, and Characterization of Two Inflammatory Proteins, Neutrophil Activating Peptide 1 (Interleukin-8) and Neutrophil Activating Peptide 2," Biochemistry, vol. 30, pp. 3128-3135, (1991).
Cotter et al., "Molecular genetic analysis of herpesviruses and their potential use as vectors for gene therapy applications," Current Opinion in Molecular Therapeutics 1(5):633-644, 1999.
Davidson et al., "Overproduction of Polyomavirus Middle T Antigen in Mammalian Cells through the Use of an Adenovirus Vector," Journal of Virology 61(4):1226-1239, Apr. 1987.
Dawson, et al., "Synthesis of Proteins by Native Chemical Ligation," Science, vol. 266, pp. 776-779, (Nov. 4, 1994).

De Lisle Milton, et al., "Synthesis of Proteins by Chemical Ligation of Unprotected Peptide Segments: Mirror-Image Enzyme Molecules, D- & L-HIV Protease Analogs," Techniques in Protein Chemistry IV, Academic Press, New York, pp. 257-267, (1992).
Dietz et al., "Delivery of bioactive molecules into the cell: the Trojan horse approach," Mol. Cell. Neurosci. 27:85-131, 2004.
Dirig, et al., "Characterization of variables defining hindpaw withdrawal latency evoked by radiant thermal stimuli," Journal of Neuroscience Methods, vol. 76, pp. 183-191, (1997).
Egleton et al., "Development of Neuropeptide Drugs that Cross the Blood-Brain Barrier," The Journal of the American Society for Experimental NeuroTherapeutics 2(1):44-53, Jan. 2005.
Extended European Search Report, dated Aug. 27, 2009, for European Patent Application No. 07717960.4, 10 pages.
Partial European Search Report, dated Dec. 5, 2012, for European Patent Application No. 12153130.5, 8 pages.
Extended European Search Report, dated Jul. 22, 2014, for European Application No. 11848811.3, 8 pages.
Extended European Search Report, dated Jun. 10, 2015, for corresponding European Application No. 14200660.0-1401, 10 pages.
European Notice of Examination dated Sep. 11, 2015, issued in corresponding European Patent Application No. 11848811.3-1456, 3 pages.
European Communication dated Nov. 4, 2015, from European Patent Office for corresponding European Patent Application No. 07717960.4, 1 page.
Felgner et al., "Lipofection: A highly efficient, lipid-mediated DNA-transfection procedure," Proc. Natl. Acad. Sci. 84:7413-7417, Nov. 1987.
Fiers et al., "Complete nucleotide sequence of SV40 DNA," Nature 273:113-120, May 11, 1978.
Gómez-Foix et al., "Adenovirus-mediated Transfer of the Muscle Glycogen Phosphorylase Gene into Hepatocytes Confers Altered Regulation of Glycogen Metabolism," The Journal of Biological Chemistry 267(35):25129-25134, Dec. 15, 1992.
Greenaway et al., "Human cytomegalovirus DNA: BamHI, EcoRI and PstI restriction endonuclease cleavage maps," Gene 18:355-360, 1982.
Guzman et al., "Efficient Gene Transfer Into Myocardium by Direct Injection of Adenovirus Vectors," Circ. Res.73:1202-1207, 1993.
Haj-Ahmad et al., "Development of a Helper-Independent Human Adenovirus Vector and Its Use in the Transfer of the Herpes Simplex Virus Thymidine Kinase Gene," Journal of Virology 57(1):267-274, Jan. 1986.
Hargreaves, et al., "A new and sensitive method for measuring thermal nociception in cutaneous hyperalgesia," Pain, vol. 32, pp. 77-88, (1988).
Hawes et al., "Galanin and galanin-like peptide modulate neurite outgrowth via protein kinase C-mediated activation of extracellular signal-related kinase," European Journal of Neuroscience 23(11):2937-2946, 2006.
Hughes et al., "Monoclonal Antibody Targeting of Liposomes to Mouse Lung in Vivo," Cancer Research 49:6214-6220, Nov. 15, 1989.
Ibba, et al., "Towards Engineering Proteins by Site-Directed Incorporation In Vivo of Non-Natural Amino Acids," Bio/Technology, vol. 12, pp. 678-682, (Jul. 1994).
Ibba, "Strategies for in vitro and in vivo translation with non-natural amino acids," Biotechnology and Genetic Engineering Reviews, vol. 13, pp. 197-216 (Dec. 1995).
Indian Office Action dated May 26, 2016, for corresponding Indian Patent Application No. 6729/DELNP/2008, 9 pages (translation only).
International Preliminary Report on Patentability, dated Jul. 8, 2008, for International Application No. PCT/US2007/000261, 8 pages.
International Search Report, dated Oct. 3, 2007, for International Application No. PCT/US2007/000261, 7 pages.
Office Action dated May 26, 2016, for corresponding Indian Patent Application No. 6729/DELNP/2008, 9 pages (translation only).
Itakura et al., "Synthesis and Use of Synthetic Oligonucleotides," Ann. Rev. Biochem. 53:323-356, 1984.

(56) References Cited

OTHER PUBLICATIONS

Kirshenbaum et al., "Highly Efficient Gene Transfer into Adult Ventricular Myocytes by Recombinant Adenovirus," J. Clin. Invest. 92:381-387, Jul. 1993.
Kroll et al., "Outwitting the Blood-Brain Barrier for Therapeutic Purposes: Osmotic Opening and Other Means," Neurosurgery 42(5):1083-1099, May 1998.
Jaeger, et al., "Improved predictions of secondary structures for RNA," Proc. Natl. Acad. Sci., vol. 86, pp. 7706-7710, (Oct. 1989).
Jaeger, et al., "Predicting Optimal and Suboptimal Secondary Structure for RNA," Methods in Enzymology, vol. 183, pp. 281-306, (1989).
Japanese Office Action for corresponding Japanese Patent Application No. 2014-85431, dated Jun. 2, 2015, 2 pages.
Japanese Office Action for corresponding Japanese Patent Application No. 2013-544755, dated Nov. 5, 2015, 7 pages.
Japanese Office Action for corresponding Japanese Patent Application No. 2014-85431, dated Jun. 2, 2016, 11 pages (with translation).
Jensen, et al., "Effects of an Intrathecal Dopamine Agonist, Apomorphine, on Thermal and Chemical Evoked Noxious Responses in Rats," Brain Research, vol. 296, No. 2, pp. 285-293, (1984).
La Salle et al., "An Adenovirus Vector for Gene Transfer into Neurons and Glia in the Brain," Science 259:988-990, Feb. 12, 1993.
Laimins et al., "Osmotic control of kdp operon expression in *Escherichia coli*," Proc. Natl. Acad. Sci. 78(1):464-468, Jan. 1981.
Langel et al., "Chemistry and Molecular Biology of Galanin Receptor Ligands," Ann NY Acad Sci 863:86-93, 1998.
Litzinger et al., "Biodistribution and immunotargetability of ganglioside-stabilized dioleoylphosphatidylethanolamine liposomes," Biochimica et Biophysica Acta 1104:179-187, 1992.
Liu et al., "Receptor subtype-specific pronociceptive and analgesic actions of galanin in the spinal cord: Selective actions via GalR1 and GalR2 receptors," PNAS 98(17):9960-9964, Aug. 14, 2001.
Lusky et al., "Bovine Papilloma Virus Contains an Activator of Gene Expression at the Distal End of the Early Transcription Unit," Molecular and Cellular Biology 3(6):1108-1122, Jun. 1983.
Maletínská et al., "Angiotensin Analogues Palmitoylated in Positions 1 and 4," J. Med. Chem. 40:3271-3279, 1997.
Massie et al., "Construction of a helper-free recombinant adenovirus that expresses polyomavirus large T antigen," Molecular and Cellular Biology 6(8):2872-2883, Aug. 1986.
Morsy et al., "Efficient Adenoviral-mediated Ornithine Transcarbamylase Expression in Deficient Mouse and Human Hepatocytes," J. Clin. Invest. 92(3):1580-1586, Sep. 1993.
Moullier et al., "Correction of lysosomal storage in the liver and spleen of MPS VII mice by implantation of genetically modified skin fibroblasts," Nature Genetics 4(2):154-159, Jun. 1993.
Mulligan et al., "Expression of a Bacterial Gene in Mammalian Cells," Science 209(4463):1422-1427, Sep. 19, 1980.
Mulligan, "The Basic Science of Gene Therapy," Science 260:926-932, May 14, 1993.
Narang et al., "Chemical Synthesis of Deoxyoligonucleotides by the Modified Triester Method," Methods in Enzymology 65:610-620, 1980.
Needleman, et al., "A General Method Applicable to the Search for Similarities in the Amino Acid Sequence of Two Proteins," J. Mol. Biol., vol. 48, pp. 443-453, (1970).
Nielsen et al., "Peptide Nucleic Acid (PNA). A DNA Mimic with a Peptide Backbone," Bioconjugate Chem. 5:3-7, 1994.
Oritz et al., "A Novel Long-Acting Selective Neuropeptide Y2 Receptor Polyethylene Glycol-Conjugated Peptide Agonist Reduces Food Intake and Body Weight and Improves Glucose Metabolism in Rodents," The Journal of Pharmacology and Experimental Therapeutics 323(2):692-700, 2007.
Osborne et al., "Transcription Control Region Within the Protein-Coding Portion of Adenovirus E1A Genes," Molecular and Cellular Biology 4(7):1293-1305, Jul. 1984.
Pearson, et al., "Improved tools for biological sequence comparison," Proc. Natl. Acad. Sci., vol. 85, pp. 2444-2448, (Apr. 1988).
Pietersz et al., "Antibody Conjugates for the Treatment of Cancer," Immunological Reviews 129:57-80, 1992.
Poduslo et al., "Polyamine Modification Increases the Permeability of Proteins at the Blood-Nerve and Blood-Brain Barriers," Journal of Neurochemistry 66:1599-1609, 1996 (1 Page Only).
Poduslo et al., "β-Sheet Breaker Peptide Inhibitor of Alzheimer's Amyloidogenesis with Increased Blood-Brain Barrier Permeability and Resistance to Proteolytic Degradation in Plasma," Journal of Neurobiology 39(3):371-382, Jun. 1999.
Pooga et al., "Novel galanin receptor ligands," J. Peptide Res. 51(1):65-74, 1998.
PubChem Open Chemistry Database, "Sarcosine—C3H7NO2," U.S. National Library of Medicine, (Sarcosine, accessed Jan. 20, 2015), 19 pages, (URL:http://www.ncbi.nlm.nih.gov/pmc/articles/PMC2765488/pdf/nihms94183.pdf).
Racine, "Modification of Seizure Activity by Electrical Stimulation: II. Motor Seizure," Electroenceph. and Clin. Neurophysiol. 32(3):281-294, 1972.
Ragot et al., "Replication-defective recombinant adenovirus expressing the Epstein-Barr virus (EBV) envelope glycoprotein gp340/220 induces protective immunity against EBV-induced lymphomas in the cottontop tamarin," Journal of General Virology 74:501-507, 1993.
Rajarathnam, et al., "$^1$H NMR Studies of Interleukin 8 Analogs: Characterization of the Domains Essential for Function," Biochemistry, vol. 33, pp. 6623-6630, (1994).
Rich et al., "Development and Analysis of Recombinant Adenoviruses for Gene Therapy of Cystic Fibrosis," Human Gene Therapy 4:461-476, 1993.
Rivera Baeza et al., "Analogs of Galanin(1-16) Modified in Positions 1-3 as Ligands to Rat Hypothalamic Galanin Receptors," Acta Chemica Scandinavica 48:434-438, 1994.
Rizo, et al., "Constrained Peptides: Models of Bioactive Peptides and Protein Substructures," Annu. Rev. Biochem., vol. 61, pp. 387-418, (1992).
Roessler et al., "Adenoviral-mediated Gene Transfer to Rabbit Synovium In Vivo," J. Clin. Invest. 92:1085-1092, Aug. 1993.
Roffler et al., "Anti-neoplastic glucuronide prodrug treatment of human tumor cells targeted with a monoclonal antibody-enzyme conjugate," Biochem. Pharmacal. 42(10):2062-2065, 1991.
Schnölzer, et al., "Constructing Proteins by Dovetailing Unprotected Synthetic Peptides: Backbone-Engineered HIV Protease," Science, vol. 256, pp. 221-225, (Apr. 10, 1992).
Saito et al., "Somatostatin regulates brain amyloid β peptide $Aβ_{42}$ through modulation of proteolytic degradation," Nature Medicine 11(4):434-439, Apr. 2005.
Senter et al., "Generation of 5-Fluorouracil from 5-Fluorocytosine by Monoclonal Antibody-Cystosine Deaminase Conjugates," Bioconjugate Chem. 2:447-451, 1991.
Senter et al., "Generation of Cytotoxic Agents by Targeted Enzymes," Bioconjugate Chem. 4(1):3-9, 1993.
Seth et al., "Evidence that the Penton Base of Adenovirus Is Involved in Potentiation of Toxicity of Pseudomonas Exotoxin Conjugated to Epidermal Growth Factor," Molecular and Cellular Biology 4(8):1528-1533, Aug. 1984.
Seth et al., "Role of Low-pH Environment in Adenovirus Enhancement of the Toxicity of a Pseudomonas Exotoxin-Epidermal Growth Factor Conjugate," Journal of Virology 51(3):650-655, Sep. 1984.
Shen et al., "(C) Means to Enhance Penetration: (3) Enhancement of polypeptide and protein absorption by macromolecular carriers via endocytosis and transcytosis," Advanced Drug Delivery Reviews 8(1):93-113, Jan. 1992.
Smith, et al., "Comparison of Biosequences," Advances in Applied Mathematics, vol. 2, pp. 482-489, (1981).
Southern et al., "Transformation of Mammalian Cells to Antibiotic Resistance with a Bacterial Gene Under Control of the SV40 Early Region Promoter," J. Mole. Appl. Genet. 1(4):327-341, 1982.
Suarez et al, "The axotomy-induced neuropeptides galanin and pituitary adenylate cyclase-activating peptide promote axonal sprouting of primary afferent and cranial motor neurones," European Journal of Neuroscience 24(6):1555-1564, 2006.

(56) References Cited

OTHER PUBLICATIONS

Sugden et al., "A Vector That Replicates as a Plasmid and Can Be Efficiently Selected in B-Lymphoblasts Transformed by Epstein-Barr Virus," Molecular and Cellular Biology 5(2):410-413, Feb. 1985.
Sun et al., "Human artificial episomal chromosomes for cloning large DNA fragments in human cells," Nature Genetics 8:33-41, Sep. 1994.
Svensson, "Role of Vesicles During Adenovirus 2 Internalization into HeLa Cells," Journal of Virology 55(2):442-449, Aug. 1985.
Thorson, et al., "A Biosynthetic Approach for the Incorporation of Unnatural Amino Acids into Proteins," Methods in Molecular Biology, vol. 77, pp. 43-73 (1998).
Taiwanese Office Action, dated Jan. 9, 2015, for corresponding Taiwanese Patent Application No. 102120233, 10 pages (with English Translation).
Tjølsen, et al., "The formalin test: an evaluation of the method," Pain, vol. 51, pp. 5-17, (1992).
Tsuji et al., "Carrier-mediated or specialized transport of drugs across the blood-brain barrier," Advanced Drug Delivery Reviews 36:277-290, 1999.
Toyobuku et al., "Delivery of Peptide Drugs to the Brain by Adenovirus-Mediated Heterologous Expression of Human Oligopeptide Transporter at the Blood-Brain Barrier," J. Pharmacal. Exp. Ther. 305(1):40-47, 2003.
Varga et al., "Infectious Entry Pathway of Adenovirus Type 2," Journal of Virology 65(11):6061-6070, Nov. 1991.
Verma, "Retroviral Vectors for Gene Transfer," American Society for Microbiology, pp. 229-232, 1985.
Vezzani et al., "Brain somatostatin: a candidate inhibitory role in seizures and epileptogenesis," European Journal of Neuroscience 11:3767-3776, 1999.
White et al., "Developing Novel Antiepileptic Drugs: Characterization of NAX 5055, a Systemically-Active Galanin Analog, in Epilepsy Models," The Journal of the American Society for Experimental NeuroTherapeutics 6(2):372-380, Apr. 2009.
Wickham et al., "Integrins $\alpha_v\beta_3$ and $\alpha_v\beta_5$ Promote Adenovirus Internalization but Not Virus Attachment," Cell 73:309-319, Apr. 23, 1993.
Witt et al., "Peptide drug modifications to enhance bioavailability and blood-brain barrier permeability," Peptides 22(12):2329-2343, 2001.
Wolff et al., "Direct Gene Transfer into Mouse Muscle in Vivo," Science 247:1465-1468, Mar. 23, 1990.
Zabner et al., "Adenovirus-Mediated Gene Transfer Transiently Corrects the Chloride Transport Defect in Nasal Epithelia of Patients with Cystic Fibrosis," Cell 75:207-216, Oct. 22, 1993.
Zabner et al., "Safety and efficacy of repetitive adenovirus-mediated transfer of CFTR cDNA to airway epithelia of primates and cotton rats," Nature Genetics 6(1):75-83, Jan. 1994.
Zoller, M.J., "New recombinant DNA methodology for protein engineering," Current Opinion in Biotechnology, vol. 3, pp. 348-354 (1992).
Zhang, "Generation and identification of recombinant adenovirus by liposome-mediated transfection and PCR analysis," BioTechniques 15:868-872, 1993.
Zhang et al., "Incorporation of Monodisperse Oligoethyleneglycol Amino Acids into Anticonvulsant Analogues of Galanin and Neuropeptide Y Provides Peripherally Acting Analgesics," Molecular Pharmaceutics 10(2):574-585, Feb. 2013.
Zhang et al., "Structural Requirements for a Lipoamino Acid in Modulating the Anticonvulsant Activities of Systemically Active Galanin Analogues," J. Med. Chem. 52:1310-1316, Mar. 2009.
Zucker, M., "On Finding All Suboptimal Foldings of an RNA Molecule," Science, vol. 244, pp. 48-52, (Apr. 7, 1989).
International Search Report and Written Opinion dated Aug. 17, 2012 in International Patent Application No. PCT/US2011/064977.
International Preliminary Report on Patentability dated Jun. 18, 2013 in International Patent Application No. PCT/US2011/064977.
Canadian Office Action issued in corresponding Canadian Patent Application No. 2,858,811, dated Nov. 7, 2017, 4 pages.
European Communication under Rule 71(3) EPC issued in corresponding European Patent Application No. 11 848 811.3-1466, dated Oct. 13, 2017, 57 pages.
Israeli Notification of Defects issued in corresponding Israeli Patent Application No. 226925, dated Aug. 10, 2017, 4 pages (English translation only).
Japanese Office Action issued in copending Japanese Patent Application No. 2014-085431, dated May 22, 2017, 3 pages (with English translation).
Japanese Office Action issued in corresponding Japanese Patent Application No. 2013-544755, dated Sep. 26, 2017, 8 pages (with English translation).
Japanese Office Action for corresponding Japanese Patent Application No. 2013-544755, dated Oct. 20, 2016, 7 pages (with English translation).
European Communication under Rule 71(3) EPC for corresponding European Application No. 11 848 811.3-1466, dated Jan. 4, 2017, 7 pages.

"Gal-93"

(SEQ ID NO: 20)

SEQUENCE LISTING

<160> NUMBER OF SEQ ID NOS: 29

<210> SEQ ID NO 1
<211> LENGTH: 30
<212> TYPE: PRT
<213> ORGANISM: Homo sapiens

<400> SEQUENCE: 1

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 2
<211> LENGTH: 36
<212> TYPE: PRT
<213> ORGANISM: Homo sapiens

<400> SEQUENCE: 2

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 3
<211> LENGTH: 13
<212> TYPE: PRT
<213> ORGANISM: Homo sapiens

<400> SEQUENCE: 3

Glx Leu Tyr Glu Asn Lys Pro Arg Arg Pro Tyr Ile Leu
1               5                   10

<210> SEQ ID NO 4
<211> LENGTH: 14
<212> TYPE: PRT
<213> ORGANISM: Homo sapiens

<400> SEQUENCE: 4

Ala Gly Cys Lys Asn Phe Phe Trp Lys Thr Phe Thr Ser Cys
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (1)..(1)
<223> OTHER INFORMATION: N-methyl-gly (Sarcosine)
<220> FEATURE:
<221> NAME/KEY: xaa
<222> LOCATION: (1)..(1)
<223> OTHER INFORMATION: Sarcosine
<220> FEATURE:
<221> NAME/KEY: xaa
<222> LOCATION: (16)..(16)
<223> OTHER INFORMATION: Lys-MPEG_4

<400> SEQUENCE: 5

Xaa Trp Thr Leu Asn Ser Ala Gly Tyr Leu Leu Gly Pro Lys Lys Xaa
1               5                   10                  15

Lys

<210> SEQ ID NO 6
<211> LENGTH: 16
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (15)..(15)
<223> OTHER INFORMATION: Lys-MPEG_4

<400> SEQUENCE: 6

Trp Thr Leu Asn Ser Ala Gly Tyr Leu Leu Gly Pro Lys Lys Xaa Lys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (1)..(1)
<223> OTHER INFORMATION: N-Methyl-Trp
<220> FEATURE:
<221> NAME/KEY: xaa
<222> LOCATION: (15)..(15)
<223> OTHER INFORMATION: Lys-MPEG_4

<400> SEQUENCE: 7

Xaa Thr Leu Asn Ser Ala Gly Tyr Leu Leu Gly Pro Lys Lys Xaa Lys
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (1)..(1)
<223> OTHER INFORMATION: Sarcosine
<220> FEATURE:
<221> NAME/KEY: xaa
<222> LOCATION: (16)..(16)
<223> OTHER INFORMATION: Lys-MPEG_12

<400> SEQUENCE: 8

Xaa Trp Thr Leu Asn Ser Ala Gly Tyr Leu Leu Gly Pro Lys Lys Xaa
1               5                   10                  15

Lys

<210> SEQ ID NO 9
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (1)..(1)
<223> OTHER INFORMATION: Sarcosine

```
<220> FEATURE:
<221> NAME/KEY: xaa
<222> LOCATION: (16)..(16)
<223> OTHER INFORMATION: Lys-Pal
<220> FEATURE:
<221> NAME/KEY: xaa
<222> LOCATION: (18)..(18)
<223> OTHER INFORMATION: Lys-MPEG_12

<400> SEQUENCE: 9

Xaa Trp Thr Leu Asn Ser Ala Gly Tyr Leu Leu Gly Pro Lys Lys Xaa
1               5                   10                  15

Lys Xaa

<210> SEQ ID NO 10
<211> LENGTH: 16
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (15)..(15)
<223> OTHER INFORMATION: Lys-MPEG_24

<400> SEQUENCE: 10

Trp Thr Leu Asn Ser Ala Gly Tyr Leu Leu Gly Pro Lys Lys Xaa Lys
1               5                   10                  15

<210> SEQ ID NO 11
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (1)..(1)
<223> OTHER INFORMATION: Sarcosine
<220> FEATURE:
<221> NAME/KEY: xaa
<222> LOCATION: (18)..(18)
<223> OTHER INFORMATION: Lys-MPEG_24

<400> SEQUENCE: 11

Xaa Trp Thr Leu Asn Ser Ala Gly Tyr Leu Leu Gly Pro Lys Lys Lys
1               5                   10                  15

Lys Xaa

<210> SEQ ID NO 12
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (1)..(1)
<223> OTHER INFORMATION: sarcosine
<220> FEATURE:
<221> NAME/KEY: xaa
<222> LOCATION: (16)..(16)
<223> OTHER INFORMATION: Lys-Pal
<220> FEATURE:
<221> NAME/KEY: xaa
<222> LOCATION: (18)..(18)
<223> OTHER INFORMATION: Lys-MPEG_24
```

```
<400> SEQUENCE: 12

Xaa Trp Thr Leu Asn Ser Ala Gly Tyr Leu Leu Gly Pro Lys Lys Xaa
1               5                   10                  15

Lys Xaa

<210> SEQ ID NO 13
<211> LENGTH: 17
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (15)..(15)
<223> OTHER INFORMATION: Lys-Pal
<220> FEATURE:
<221> NAME/KEY: xaa
<222> LOCATION: (17)..(17)
<223> OTHER INFORMATION: Lys-MPEG_24

<400> SEQUENCE: 13

Trp Thr Leu Asn Ser Ala Gly Tyr Leu Leu Gly Pro Lys Lys Xaa Lys
1               5                   10                  15

Xaa

<210> SEQ ID NO 14
<211> LENGTH: 18
<212> TYPE: PRT
<213> ORGANISM: Artificial Sequence
<220> FEATURE:
<223> OTHER INFORMATION: Nueropeptide analog
<220> FEATURE:
<221> NAME/KEY: xaa
<222> LOCATION: (1)..(1)
<223> OTHER INFORMATION: Sarcosine
<220> FEATURE:
<221> NAME/KEY: xaa
<222> LOCATION: (16)..(16)
<223> OTHER INFORMATION: Lys-alpha-Linolenic acid
<220> FEATURE:
<221> NAME/KEY: xaa
<222> LOCATION: (18)..(18)
<223> OTHER INFORMATION: Lys-MPEG_24

<400> SEQUENCE: 14

Xaa Trp Thr Leu Asn Ser Ala Gly Tyr Leu Leu Gly Pro Lys Lys Xaa
1               5                   10                  15

Lys Xaa

<210> SEQ ID NO 15
<211> LENGTH: 17
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (15)..(15)
<223> OTHER INFORMATION: Lys-alpha-Linolenic acid
<220> FEATURE:
<221> NAME/KEY: xaa
<222> LOCATION: (17)..(17)
<223> OTHER INFORMATION: Lys-MPEG_24

<400> SEQUENCE: 15

Trp Thr Leu Asn Ser Ala Gly Tyr Leu Leu Gly Pro Lys Lys Xaa Lys
1               5                   10                  15

Xaa
```

```
<210> SEQ ID NO 16
<211> LENGTH: 17
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (1)..(1)
<223> OTHER INFORMATION: Sarcosine
<220> FEATURE:
<221> NAME/KEY: xaa
<222> LOCATION: (16)..(16)
<223> OTHER INFORMATION: Lys-MPEG_24

<400> SEQUENCE: 16

Xaa Trp Thr Leu Asn Ser Ala Gly Tyr Leu Leu Gly Pro Lys Lys Xaa
1               5                   10                  15

Lys

<210> SEQ ID NO 17
<211> LENGTH: 18
<212> TYPE: PRT
<213> ORGANISM: Artificial Sequence
<220> FEATURE:
<223> OTHER INFORMATION: Nueropeptide analog
<220> FEATURE:
<221> NAME/KEY: xaa
<222> LOCATION: (4)..(4)
<223> OTHER INFORMATION: Lys-MPEG_24
<220> FEATURE:
<221> NAME/KEY: xaa
<222> LOCATION: (5)..(5)
<223> OTHER INFORMATION: aminohexanoic acid

<400> SEQUENCE: 17

Tyr Lys Lys Xaa Xaa Ala Arg His Tyr Ile Asn Leu Ile Thr Arg Gln
1               5                   10                  15

Arg Tyr

<210> SEQ ID NO 18
<211> LENGTH: 8
<212> TYPE: PRT
<213> ORGANISM: Artificial Sequence
<220> FEATURE:
<223> OTHER INFORMATION: Neuropeptide analog
<220> FEATURE:
<221> NAME/KEY: xaa
<222> LOCATION: (2)..(2)
<223> OTHER INFORMATION: Lys-MPEG_24

<400> SEQUENCE: 18

Lys Xaa Lys Lys Pro Tyr Ile Leu
1               5

<210> SEQ ID NO 19
<211> LENGTH: 18
<212> TYPE: PRT
<213> ORGANISM: Artificial Sequence
<220> FEATURE:
<223> OTHER INFORMATION: Nuropeptide analog
<220> FEATURE:
<221> NAME/KEY: xaa
<222> LOCATION: (1)..(1)
<223> OTHER INFORMATION: Sarcosine
<220> FEATURE:
<221> NAME/KEY: xaa
<222> LOCATION: (16)..(16)
<223> OTHER INFORMATION: Lys-Pal
```

```
<220> FEATURE:
<221> NAME/KEY: xaa
<222> LOCATION: (18)..(18)
<223> OTHER INFORMATION: Lys-MPEG_24-NH-PEG_24

<400> SEQUENCE: 19

Xaa Trp Thr Leu Asn Ser Ala Gly Tyr Leu Leu Gly Pro Lys Lys Xaa
1               5                   10                  15

Lys Xaa

<210> SEQ ID NO 20
<211> LENGTH: 17
<212> TYPE: PRT
<213> ORGANISM: Artificial Sequence
<220> FEATURE:
<223> OTHER INFORMATION: Neuropeptide analog
<220> FEATURE:
<221> NAME/KEY: VARIANT
<222> LOCATION: 17
<223> OTHER INFORMATION: Xaa = Lys-MPEG_24

<400> SEQUENCE: 20

Trp Thr Leu Asn Ser Ala Gly Tyr Leu Leu Gly Pro Lys Lys Lys Lys
1               5                   10                  15

Xaa

<210> SEQ ID NO 21
<211> LENGTH: 19
<212> TYPE: PRT
<213> ORGANISM: Artificial Sequence
<220> FEATURE:
<223> OTHER INFORMATION: Neuropeptide analog
<220> FEATURE:
<221> NAME/KEY: VARIANT
<222> LOCATION: 1
<223> OTHER INFORMATION: Xaa = Ac
<220> FEATURE:
<221> NAME/KEY: VARIANT
<222> LOCATION: 5
<223> OTHER INFORMATION: Xaa = Lys-MPEG_24
<220> FEATURE:
<221> NAME/KEY: VARIANT
<222> LOCATION: 6
<223> OTHER INFORMATION: Xaa = aminohexanoic acid

<400> SEQUENCE: 21

Xaa Tyr Lys Lys Xaa Xaa Ala Arg His Tyr Ile Asn Leu Ile Thr Arg
1               5                   10                  15

Gln Arg Tyr

<210> SEQ ID NO 22
<211> LENGTH: 9
<212> TYPE: PRT
<213> ORGANISM: Artificial Sequence
<220> FEATURE:
<223> OTHER INFORMATION: Neuropeptide analog
<220> FEATURE:
<221> NAME/KEY: VARIANT
<222> LOCATION: 1
<223> OTHER INFORMATION: Xaa = Ac
<220> FEATURE:
<221> NAME/KEY: VARIANT
<222> LOCATION: 3
<223> OTHER INFORMATION: Xaa = Lys-MPEG_24

<400> SEQUENCE: 22

Xaa Lys Xaa Lys Lys Pro Tyr Ile Leu
1               5
```

```
<210> SEQ ID NO 23
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: MOD_RES
<222> LOCATION: 1
<223> OTHER INFORMATION: Xaa = Sar-Boc
<220> FEATURE:
<221> NAME/KEY: MOD_RES
<222> LOCATION: 2
<223> OTHER INFORMATION: Xaa = Trp-Boc
<220> FEATURE:
<221> NAME/KEY: MOD_RES
<222> LOCATION: 3
<223> OTHER INFORMATION: Xaa = Thr-But
<220> FEATURE:
<221> NAME/KEY: MOD_RES
<222> LOCATION: 5
<223> OTHER INFORMATION: Xaa = Asn-Trt
<220> FEATURE:
<221> NAME/KEY: MOD_RES
<222> LOCATION: 6
<223> OTHER INFORMATION: Xaa = Ser-But
<220> FEATURE:
<221> NAME/KEY: MOD_RES
<222> LOCATION: 9
<223> OTHER INFORMATION: Xaa = Tyr-But
<220> FEATURE:
<221> NAME/KEY: MOD_RES
<222> LOCATION: (14)...(15)
<223> OTHER INFORMATION: Xaa = Lys-Boc
<220> FEATURE:
<221> NAME/KEY: MOD_RES
<222> LOCATION: 16
<223> OTHER INFORMATION: Xaa = Lys-Pal
<220> FEATURE:
<221> NAME/KEY: MOD_RES
<222> LOCATION: 17
<223> OTHER INFORMATION: Xaa = Lys-Boc
<220> FEATURE:
<221> NAME/KEY: MOD_RES
<222> LOCATION: 18
<223> OTHER INFORMATION: Xaa = Lys-(Sieber resin)(4-methoxytrityl)

<400> SEQUENCE: 23

Xaa Xaa Xaa Leu Xaa Xaa Ala Gly Xaa Leu Leu Gly Pro Xaa Xaa Xaa
1               5                   10                  15

Xaa Xaa

<210> SEQ ID NO 24
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: MOD_RES
<222> LOCATION: 1
<223> OTHER INFORMATION: Xaa = Sar-Boc
<220> FEATURE:
<221> NAME/KEY: MOD_RES
<222> LOCATION: 2
<223> OTHER INFORMATION: Xaa = Trp-Boc
<220> FEATURE:
<221> NAME/KEY: MOD_RES
<222> LOCATION: 3
<223> OTHER INFORMATION: Xaa = Thr-But
<220> FEATURE:
<221> NAME/KEY: MOD_RES
<222> LOCATION: 5
<223> OTHER INFORMATION: Xaa = Asn-Trt
```

```
<220> FEATURE:
<221> NAME/KEY: MOD_RES
<222> LOCATION: 6
<223> OTHER INFORMATION: Xaa = Ser-But
<220> FEATURE:
<221> NAME/KEY: MOD_RES
<222> LOCATION: 9
<223> OTHER INFORMATION: Xaa = Tyr-But
<220> FEATURE:
<221> NAME/KEY: MOD_RES
<222> LOCATION: (14)...(15)
<223> OTHER INFORMATION: Xaa = Lys-Boc
<220> FEATURE:
<221> NAME/KEY: MOD_RES
<222> LOCATION: 16
<223> OTHER INFORMATION: Xaa = Lys-Pal
<220> FEATURE:
<221> NAME/KEY: MOD_RES
<222> LOCATION: 17
<223> OTHER INFORMATION: Xaa = Lys-Boc

<400> SEQUENCE: 24

Xaa Xaa Xaa Leu Xaa Xaa Ala Gly Xaa Leu Leu Gly Pro Xaa Xaa Xaa
1               5                   10                  15

Xaa Lys

<210> SEQ ID NO 25
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: MOD_RES
<222> LOCATION: 1
<223> OTHER INFORMATION: Xaa = Sar-Boc
<220> FEATURE:
<221> NAME/KEY: MOD_RES
<222> LOCATION: 2
<223> OTHER INFORMATION: Xaa = Trp-Boc
<220> FEATURE:
<221> NAME/KEY: MOD_RES
<222> LOCATION: 3
<223> OTHER INFORMATION: Xaa = Thr-But
<220> FEATURE:
<221> NAME/KEY: MOD_RES
<222> LOCATION: 5
<223> OTHER INFORMATION: Xaa = Asn-Trt
<220> FEATURE:
<221> NAME/KEY: MOD_RES
<222> LOCATION: 6
<223> OTHER INFORMATION: Xaa = Ser-But
<220> FEATURE:
<221> NAME/KEY: MOD_RES
<222> LOCATION: 9
<223> OTHER INFORMATION: Xaa = Tyr-But
<220> FEATURE:
<221> NAME/KEY: MOD_RES
<222> LOCATION: (14)...(15)
<223> OTHER INFORMATION: Xaa = Lys-Boc
<220> FEATURE:
<221> NAME/KEY: MOD_RES
<222> LOCATION: 16
<223> OTHER INFORMATION: Xaa = Lys-Pal
<220> FEATURE:
<221> NAME/KEY: MOD_RES
<222> LOCATION: 17
<223> OTHER INFORMATION: Xaa = Lys-Boc
<220> FEATURE:
<221> NAME/KEY: MOD_RES
<222> LOCATION: 18
<223> OTHER INFORMATION: Xaa = Lys-Sieber resin
```

```
<400> SEQUENCE: 25

Xaa Xaa Xaa Leu Xaa Xaa Ala Gly Xaa Leu Leu Gly Pro Xaa Xaa Xaa
1               5                   10                  15

Xaa Xaa

<210> SEQ ID NO 26
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: MOD_RES
<222> LOCATION: 1
<223> OTHER INFORMATION: Xaa = Sar
<220> FEATURE:
<221> NAME/KEY: MOD_RES
<222> LOCATION: 16
<223> OTHER INFORMATION: Xaa = Lys-Pal
<220> FEATURE:
<221> NAME/KEY: MOD_RES
<222> LOCATION: 18
<223> OTHER INFORMATION: Xaa = Lys-MPEG_n

<400> SEQUENCE: 26

Xaa Trp Thr Leu Asn Ser Ala Gly Tyr Leu Leu Gly Pro Lys Lys Xaa
1               5                   10                  15

Lys Xaa

<210> SEQ ID NO 27
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: MOD_RES
<222> LOCATION: 1
<223> OTHER INFORMATION: Xaa = Sar-Boc
<220> FEATURE:
<221> NAME/KEY: MOD_RES
<222> LOCATION: 2
<223> OTHER INFORMATION: Xaa = Trp-Boc
<220> FEATURE:
<221> NAME/KEY: MOD_RES
<222> LOCATION: 3
<223> OTHER INFORMATION: Xaa = Thr-But
<220> FEATURE:
<221> NAME/KEY: MOD_RES
<222> LOCATION: 5
<223> OTHER INFORMATION: Xaa = Asn-Trt
<220> FEATURE:
<221> NAME/KEY: MOD_RES
<222> LOCATION: 6
<223> OTHER INFORMATION: Xaa = Ser-But
<220> FEATURE:
<221> NAME/KEY: MOD_RES
<222> LOCATION: 9
<223> OTHER INFORMATION: Xaa = Tyr-But
<220> FEATURE:
<221> NAME/KEY: MOD_RES
<222> LOCATION: (14)...(15)
<223> OTHER INFORMATION: Xaa = Lys-Boc
<220> FEATURE:
<221> NAME/KEY: MOD_RES
<222> LOCATION: 16
<223> OTHER INFORMATION: Xaa = Lys-allyl formate
<220> FEATURE:
<221> NAME/KEY: MOD_RES
<222> LOCATION: 17
<223> OTHER INFORMATION: Xaa = Lys-Boc
```

```
<220> FEATURE:
<221> NAME/KEY: MOD_RES
<222> LOCATION: 18
<223> OTHER INFORMATION: Xaa = Lys-(Rink amide resin)(4-methoxytrityl)

<400> SEQUENCE: 27

Xaa Xaa Xaa Leu Xaa Xaa Ala Gly Xaa Leu Leu Gly Pro Xaa Xaa Xaa
1               5                   10                  15

Xaa Xaa

<210> SEQ ID NO 28
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: MOD_RES
<222> LOCATION: 1
<223> OTHER INFORMATION: Xaa = Sar-Boc
<220> FEATURE:
<221> NAME/KEY: MOD_RES
<222> LOCATION: 2
<223> OTHER INFORMATION: Xaa = Trp-Boc
<220> FEATURE:
<221> NAME/KEY: MOD_RES
<222> LOCATION: 3
<223> OTHER INFORMATION: Xaa = Thr-Bu
<220> FEATURE:
<221> NAME/KEY: MOD_RES
<222> LOCATION: 5
<223> OTHER INFORMATION: Xaa = Asn-Trt
<220> FEATURE:
<221> NAME/KEY: MOD_RES
<222> LOCATION: 6
<223> OTHER INFORMATION: Xaa = Ser-But
<220> FEATURE:
<221> NAME/KEY: MOD_RES
<222> LOCATION: 9
<223> OTHER INFORMATION: Xaa = Tyr-But
<220> FEATURE:
<221> NAME/KEY: MOD_RES
<222> LOCATION: (14)...(15)
<223> OTHER INFORMATION: Xaa = Lys-Boc
<220> FEATURE:
<221> NAME/KEY: MOD_RES
<222> LOCATION: 16
<223> OTHER INFORMATION: Xaa = Lys-allyl formate
<220> FEATURE:
<221> NAME/KEY: MOD_RES
<222> LOCATION: 17
<223> OTHER INFORMATION: Xaa = Lys-Boc
<220> FEATURE:
<221> NAME/KEY: MOD_RES
<222> LOCATION: 18
<223> OTHER INFORMATION: Xaa = Lys-(Rink amide resin)(MPEG_24)

<400> SEQUENCE: 28

Xaa Xaa Xaa Leu Xaa Xaa Ala Gly Xaa Leu Leu Gly Pro Xaa Xaa Xaa
1               5                   10                  15

Xaa Xaa

<210> SEQ ID NO 29
<211> LENGTH: 18
<212> TYPE: PRT
<213> ORGANISM: Artificial Sequence
<220> FEATURE:
<223> OTHER INFORMATION: Neuropeptide analog
<220> FEATURE:
<221> NAME/KEY: MOD_RES
<222> LOCATION: 1
<223> OTHER INFORMATION: Xaa = Sar-Boc
```

```
<220> FEATURE:
<221> NAME/KEY: MOD_RES
<222> LOCATION: 2
<223> OTHER INFORMATION: Xaa = Trp-Boc
<220> FEATURE:
<221> NAME/KEY: MOD_RES
<222> LOCATION: 3
<223> OTHER INFORMATION: Xaa = Thr-But
<220> FEATURE:
<221> NAME/KEY: MOD_RES
<222> LOCATION: 5
<223> OTHER INFORMATION: Xaa = Asn-Trt
<220> FEATURE:
<221> NAME/KEY: MOD_RES
<222> LOCATION: 6
<223> OTHER INFORMATION: Xaa = Ser-But
<220> FEATURE:
<221> NAME/KEY: MOD_RES
<222> LOCATION: 9
<223> OTHER INFORMATION: Xaa = Tyr-But
<220> FEATURE:
<221> NAME/KEY: MOD_RES
<222> LOCATION: (14)...(15)
<223> OTHER INFORMATION: Xaa = Lys-Boc
<220> FEATURE:
<221> NAME/KEY: MOD_RES
<222> LOCATION: 16
<223> OTHER INFORMATION: Xaa = Lys-alpha-Linolenic acid
<220> FEATURE:
<221> NAME/KEY: MOD_RES
<222> LOCATION: 17
<223> OTHER INFORMATION: Xaa = Lys-Boc
<220> FEATURE:
<221> NAME/KEY: MOD_RES
<222> LOCATION: 18
<223> OTHER INFORMATION: Xaa = Lys-(Rink amide resin)(MPEG_24)

<400> SEQUENCE: 29

Xaa Xaa Xaa Leu Xaa Xaa Ala Gly Xaa Leu Leu Gly Pro Xaa Xaa Xaa
1               5                   10                  15

Xaa Xaa
```

NEUROPEPTIDE ANALOGS, COMPOSITIONS, AND METHODS FOR TREATING PAIN

CROSS-REFERENCE TO RELATED APPLICATIONS

This application is a divisional of U.S. application Ser. No. 13/994,675, filed Aug. 26, 2013, which is a U.S. National Stage of Application No. PCT/US2011/064977, filed Dec. 14, 2011, which claims the benefit of Provisional Application No. 61/423,530, filed Dec. 15, 2010, all of which are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 700172_402D1_SEQUENCE LISTING. The text file is 13.9 KB, was created on Sep. 6, 2016, and is being submitted electronically via EFS-Web.

DETAILED DESCRIPTION

Figure 1:
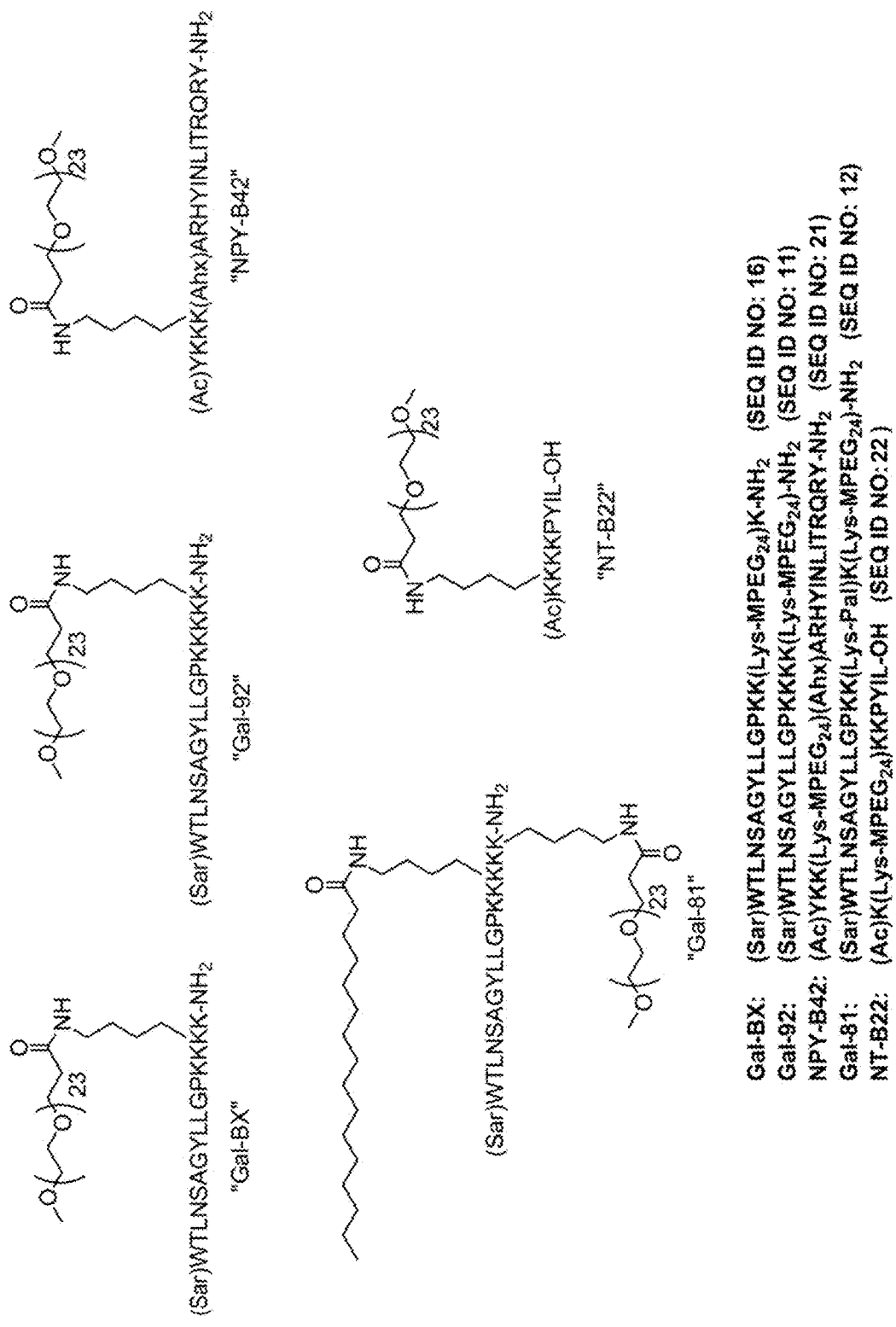
FIG. 1 shows the structures of analogs of MEGylated neuropeptide analogs according to the present description.

Neuropeptide analogs are described herein. In certain examples, neuropeptide analogs such as analogs of galanin, neuropeptide Y, somatostatin, and neurotensin are described herein. In other particular embodiments, the analogs described herein exhibit favorable pharmacological characteristics. For example, in certain such embodiments, the neuropeptide analogs described herein are metabolically stable. In other such embodiments, neuropeptide analogs exhibit activity in the peripheral nervous system when administered systemically, but do not show significant activity in the central nervous system. In still other embodiments, neuropeptide analogs described herein do not exhibit cardiovascular toxicity. In yet further such embodiments, the neuropeptide analogs described herein provide an analgesic effect. In specific embodiments, neuropeptide analogs disclosed herein exhibit one or all of the following characteristics: metabolic stability; activity in the peripheral nervous system when administered systemically combined with a lack of measurable activity in the central nervous system; a lack of cardiovascular toxicity; and an analgesic effect. In specific embodiments, neuropeptide analogs described herein comprise at least one amino acid attached to a monodisperse oligoethylene glycol unit (i.e., a MEGylated amino acid, or MEG-AA).

In addition to neuropeptide analogs, compositions and methods including such analogs are described herein. For example, in particular embodiments, analgesic compositions including one or more neuropeptide analog according to the present description are provided, and methods of using such analgesic compositions are described herein. In particular embodiments, methods of treating pain are provided, with such methods including administering a therapeutically effective amount of an analgesic composition comprising a neuropeptide analog as described herein to a subject in need thereof.

It is understood that when combinations, subsets, interactions, groups, etc. of these compositions and methods are disclosed, that while specific reference of each various individual and collective combinations and permutation of these compositions may not be explicitly disclosed, each is specifically contemplated and described herein. For example, if a polypeptide is disclosed and discussed and a number of modifications that can be made to a number of molecules including the polypeptide are discussed, each and every combination and permutation of polypeptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C, D, E, and F, and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C, D, E, and F, and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It is understood that the disclosed methods and compositions are not limited to the particular methodology, protocols, and reagents described, as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the meanings that would be commonly understood by one of skill in the art in the context of the present specification.

It must be noted that as used herein and in the appended claims, the singular forms "a," "an," and "the" include plural reference unless the context clearly dictates otherwise. Thus, for example, reference to "a peptide" includes a plurality of such peptides; reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As the terms are used herein, "protein" and "peptide" are used simply refer to polypeptide molecules generally and are not used to refer to polypeptide molecules of any specific size, length or molecular weight. Protein variants and derivatives are well understood to those of skill in the art and can involve amino acid sequence modifications. Amino acid substitutions may include one or more residues and can occur at a number of different locations at once. Substitutions, deletions, insertions or any combination thereof may be combined to arrive at a final construct. Substitutional variants are those in which at least one residue has been removed and a different residue inserted in its place.

It is understood that, as discussed herein, the use of the terms "homology" and "identity" mean the same thing as "similarity." Thus, for example, if the use of the word homology is used between two sequences it is understood that this is not necessarily indicating an evolutionary relationship between these two sequences, but rather refers to the percent similarity or relatedness between their nucleic acid sequences. For example, a peptide may have at least approximately 60%, 65%, 70%, 75%, 80%, 85%, 90%, 95%, and 99% homology with a reference amino acid sequence. Many of the methods for determining homology between two evolutionarily related molecules are routinely applied to any two or more nucleic acid sequences or amino acid sequences for the purpose of measuring sequence identity or similarity, regardless of whether such molecules are evolutionarily related.

It is understood that one way to define the, analogs, variants, and derivatives of the MEGylated neuropeptide analogs disclosed herein is through defining the analogs, variants, and derivatives in terms of identity to specific known, native, and unmodified peptide sequences or their analogs not containing MEG-AA. Disclosed herein are neuropeptide analogs having at least 40, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to a reference amino acid sequence or the native amino acid sequence, such as, for purposes of example only, an unmodified galanin polypeptide sequence (e.g., SEQ ID NO: 1), and wherein the neuropeptide analog comprises at least one, at least two, at least three, at least four, at least five, or at least six or more of any of the substitutions, deletions, additions, or extensions disclosed herein.

Methods of calculating percentage identity of one or more nucleotide or polypeptide sequences are known by those of skill in the art. For example, the percent identity can be calculated after aligning the two sequences so that the identity is at its highest level. Another way of calculating sequence similarity or identity can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity and similarity can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989, which are herein incorporated by reference for at least material related to nucleic acid alignment. It is understood that any of the methods typically can be used, and that in certain instances, the results of these various methods may differ, but the skilled artisan understands if identity is found with at least one of these methods, the sequences would be said to have the stated identity, and be disclosed herein.

Substantial changes in peptide function or immunological identity may be made by selecting amino acid substitutions that differ in their effect on maintaining, for example, (a) the structure of the polypeptide backbone in the area of the substitution, for example as a sheet or helical conformation, (b) the charge or hydrophobicity of the molecule at the target site or (c) the bulk of the side chain. The substitutions which may produce changes in the protein properties can include those in which (a) a hydrophilic residue, e.g. seryl or threonyl, is substituted for (or by) a hydrophobic residue, e.g. leucyl, isoleucyl, phenylalanyl, valyl or alanyl, (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl, or (d) a residue having a bulky side chain, e.g., phenylalanine, is substituted for (or by) one not having a side chain, e.g., glycine, in this case, (e) by increasing the number of sites for sulfation and/or glycosylation.

As this specification discusses various proteins and protein sequences, it is understood that the nucleic acids that can encode those protein sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

D-amino acids can be used to generate more stable peptides, because D-amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

The term "neuropeptide" as used herein is used to refer to several types of polypeptide molecules found in neural tissues including those found in the brain, the spinal cord, and the gut. Neuropeptides are involved in many nerve functions including analgesia, nociception, waking and sleep regulation, cognition, feeding, regulation of mood, and regulation of blood, etc. Examples of specific neuropeptides are galanin, neuropeptide Y, neurotensin, and somatostatin. Galanin is a 30-amino acid neuropeptide encoded by the GAL gene and is expressed in the CNS and other tissues of humans and other mammals (see, e.g., SEQ ID NO: 1). Neuropeptide Y is a 36-amino acid neuropeptide encoded by the NPY gene and found in many tissues of the body including the nervous system (see e.g., SEQ ID NO: 2). Neurotensin is a 13-amino acid neuropeptide found in the nervous system and the gut (see, e.g., SEQ ID NO: 3). Somatostatin is a neuropeptide with a 14-amino acid form and is expressed in the nervous system and the gut (see, e.g., SEQ ID NO: 4).

The neuropeptide analogs described herein have at least one MEGylated amino acid. A MEGylated amino acid, as used herein, denotes the attachment of at least one monodisperse oligoethylene glycol unit to an amino acid side chain of a peptide. In certain embodiments, one or more amino acids included in the reference amino acid sequence of a neuropeptide are substituted with a MEGylated amino acid. In some embodiments, at least one amino acid included in the reference amino acid sequence of the neuropeptide is modified such that it is covalently linked with one or more monodisperse oligoethylene glycol units. Examples of neuropeptides and analogs thereof that may be MEGylated as disclosed herein may be found in U.S. Patent Application Publication No. US 2009/0281031, the entirety of which is incorporated herein by reference. More specifically, examples of neuropeptides that may be MEGylated as disclosed herein comprise galanin, neuropeptide Y, neurotensin, and somatostatin.

The process of MEGylation as described herein is the process of covalently attaching a monodispersed oligoethylene glycol to an amino acid of a peptide. MEGylation as used herein is also meant to include PEGylation. In one embodiment, MEGylation as disclosed herein may include the attachment of one or more monodispersed polyethylene glycol (MPEG) units to one or more amino acids in a peptide. In certain embodiments, the MEGylation process disclosed herein is similar to the process of PEGylation, a process that is well known by those of skill in the art.

The at least one monodisperse oligoethylene glycol unit used to form a MEGylated amino acid, as included in the neuropeptide analogs disclosed herein, includes 2 or more ethylene glycol repeats. In one embodiment, a neuropeptide analog according to the present disclosure may include one or more amino acids having a monodisperse oligoethylene glycol unit comprising at least 2 to 48 ethylene glycol repeats. In one such embodiment, a neuropeptide analog may include one or more MEGylated amino acids, wherein each MEGylated amino acid comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 46, 47, and 48 or more ethylene glycol repeats. In another embodiment, the neuropeptide analogs disclosed herein may comprise a MEGylated amino acid having a monodisperse oligoethylene glycol unit comprising from 2 to 48 monodispersed polyethylene glycol ($MPEG_{n=2-48}$) repeats. In one such embodiment, a neuropeptide analog as described herein may comprise at least one MEGylated amino acid having a monodisperse polyethylene glycol unit that includes at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, and 48 MPEG repeats.

A neuropeptide analog as provided herein may be MEGylated at one or more of any of its amino acid positions. In one embodiment, a galanin analog as provided herein may be MEGylated at one or more of the amino acid positions of the galanin neuropeptide. In a particular embodiment, the galanin analog may be MEGylated at any one of amino acid positions 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, as numbered from N-(amino) terminus to C-(carboxy) terminus of the galanin analog. In certain embodiments, a neurotensin analog as provided herein may be MEGylated at any one of the amino acid positions of the neurotensin analog. More specifically, the neurotensin analog may be MEGylated at any one of amino acid positions 1, 2, 3, 4, 5, 6, 7, 8, 9, 10, 11, 12, and 13. In another embodiment, a neuropeptide Y analog as provided herein may be MEGylated at any one of the amino acid positions of the neuropeptide Y analog. In one such embodiment, the neuropeptide Y analog may be MEGylated at any one of amino acid positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and 36. In yet another embodiment, a somatostatin analog, such as the native peptide or its non-natural analogs, for example octreotide, may be MEGylated at one or more of the amino acid positions of the somatostatin neuropeptide. In a particular embodiment, the somatostatin analog may be MEGylated at any one of amino acid positions 1, 2, 3, 4, 5, 6, 7, 8, 9, 10, 11, 12, 13, and 14.

In certain embodiments, the neuropeptide analogs as disclosed herein may be MEGylated at one or more amino acids located in the C-terminus, the N-terminus, or optionally in the C-terminus and the N-terminus of the neuropeptide. In particular embodiments, the MEGylated neuropeptide analog may comprise a full-length peptide or, alternatively, a truncated peptide, wherein any one of the amino acids in the peptide may be MEGylated.

In one embodiment, a truncated galanin analog, such as, by way of example only, the galanin analog of SEQ ID NO: 5 can be used with the compositions and methods disclosed herein. In another embodiment, a truncated galanin analog may comprise a Gly$^1$ residue that has been replaced by N-methyl-Gly (sarcosine, SAR). The N-methylation of Gly$^1$ may protect the peptide from accelerated proteolytic degradation from the N-terminus, thereby improving the metabolic stability of the galanin analog. In another embodiment, a truncated galanin analog, such as a galanin analog as described herein, such as, by way of example only, the galanin analog of SEQ ID NO: 6, may comprise a C-terminal extension or addition.

In one embodiment, the MEGylated neuropeptide analogs as disclosed herein may include one or more terminal lysine (Lys), homo-Lys, and/or ornithine amino acids. In certain embodiments, the MEGylated neuropeptide analogs described herein include one or more terminal Lys amino acids. In one such embodiment, the neuropeptide analog may comprise 1, 2, 3, 4, 5, 6, 7, 8, 9, or 10 or more Lys amino acids at the C-terminus of the galanin analog. In another such embodiment of a galanin analog as described herein, the one or more terminal Lys amino acids may comprise a monodispersed oligoethylene glycol unit covalently attached to the one or more terminal Lys amino acids.

In certain embodiments, the neuropeptide analog disclosed herein is a MEGylated galanin analog including at least 1, 2, 3, 4, 5, 6, 7, 8, 9, or 10 or more Lys amino acids at the C-terminus of the galanin analog. In one such embodiment, the one or more terminal Lys amino acids may comprise a monodispersed oligoethylene glycol unit covalently attached to the one or more terminal Lys amino acids.

In other certain embodiments, the neuropeptide analog disclosed herein is a MEGylated neuropeptide Y analog including at least 1, 2, 3, 4, 5, 6, 7, 8, 9, or 10 or more Lys amino acids at the N-terminus of the neuropeptide Y analog. In one such embodiment, the one or more terminal Lys amino acids may comprise a monodispersed oligoethylene glycol unit covalently attached to the one or more terminal Lys amino acids (see, e.g., SEQ ID NO: 21 in FIG. 1).

In still other certain embodiments, the neuropeptide analog disclosed herein is a MEGylated neurotensin analog including at least 1, 2, 3, 4, 5, 6, 7, 8, 9, or 10 or more Lys amino acids at the C-terminus of the neurotensin analog. In one such embodiment, the one or more terminal Lys amino acids may comprise a monodispersed oligoethylene glycol unit covalently attached to the one or more terminal Lys amino acids (see, e.g., SEQ ID NO: 22 in FIG. 1).

Also disclosed herein are neuropeptide analogs comprising amino acid substitutions and additions, wherein the substitution or addition is of a naturally or non-naturally occurring substance. Examples include, but are not limited to, sarcosine (Sar), diaminobutyric acid (DAB), diaminopropionic acid (DAP), Lys-palmityoyl (Lys-Palm), Lys-α-Linolenic acid (Lys-α-Lnn), Chloro-phe, aminohexanoic acid (AHX), perfluorohexanoic acid (PerFHX), 8-amino-3,6,-dioxaoctanic acid, oligo-Lys, and tert-leucine.

In particular embodiments, the neuropeptide analogs disclosed herein are metabolically stable. As used herein, the terms "metabolic stability" and "metabolically stable" refer to a neuropeptide analog that is more resistant to degradation and has a longer circulating half-life when compared with a reference sequence, the wild type peptide, non-altered, unmodified, or native peptide, or with a control composition. For example, the rate of increased metabolic stability, as measured by half-life in serum or in vitro, can be 1, 2, 3, 4, 5, 6, 7, 8, 9, 10, 11, 12, 13, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 percent when compared with the control, unmodified, native, or wild-type neuropeptide or composition.

In certain embodiments, MEGylated neuropeptide analogs as disclosed herein exhibit activity in the peripheral nervous system but exhibit no measurable central nervous system activity or penetration of the blood brain barrier. For example, in certain embodiments, the neuropeptide analogs described herein exhibit analgesic activity when administered systemically, while exhibiting no measurable central nervous system activity or penetration of the blood brain barrier. Without being bound by a particular theory, it is presently thought that MEGylation of the amino acid side chains of the neuropeptide analogs described herein prevents the neuropeptide analog from crossing the blood brain barrier and acting on the central nervous system. Therefore, such neuropeptide analogs reduce or eliminate potential toxicity or side effects associated with penetration into the CNS. In particular embodiments, the ability of a peptide to penetrate the blood brain barrier may be assessed using an in-vivo model of epilepsy.

Methods for producing the neuropeptide analogs described herein are provided. For certain embodiments of the MEGylated neuropeptide analogs described herein, the modification of amino acids as disclosed herein can be introduced during solid-phase peptide synthesis using an automated peptide synthesizer. In one such embodiment, a method of producing the disclosed neuropeptide analogs includes linking two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). One skilled in the art can readily appreciate that a peptide or polypeptide corresponding to the disclosed neuropeptide analogs, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a protein, or fragment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Optionally, the peptide or polypeptide may be independently synthesized in vivo. Once isolated, these independent peptides or polypeptides may be linked to form a peptide or fragment thereof via similar peptide condensation reactions.

In another embodiment, the MEGylated neuropeptide analogs may be synthesized according to enzymatic ligation of cloned or synthetic peptide segments, thereby allowing relatively short peptide fragments to be joined to produce larger peptide fragments, polypeptides or whole protein domains (Abrahmsen L et al., Biochemistry, 30:4151 (1991)). Optionally, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini Metal. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Optionally, MEGylated neuropeptide analogs may be produced according to the process wherein unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Analgesic compositions can be prepared to include one or more neuropeptide analogs according to the present description. In particular embodiments, the analgesic compositions described herein are provided as pharmaceutical compositions, and can include, for example, one or more MEGylated neuropeptide analogs as described herein in combination with a pharmaceutically acceptable carrier. In one such embodiment, an analgesic composition as disclosed herein may include a MEGylated galanin analog. In another such embodiment, an analgesic composition as disclosed herein may include a MEGylated neuropeptide Y analog. In yet another such embodiment, an analgesic composition as disclosed herein may include a MEGylated neurotensin analog. In still another embodiment, an analgesic composition as disclosed herein may include a MEGylated somatostatin analog.

As used herein, the term "pharmaceutically acceptable" refers to a material that is not biologically or otherwise undesirable, i.e., the material may be administered to a subject, without causing any undesirable biological effects or interacting in a deleterious manner with any of the other components of the pharmaceutical composition in which it is contained. Examples of carriers suitable for administration to human and animal subjects include solutions such as sterile water, saline, and buffered solutions at physiological pH. The carrier would naturally be selected to minimize any degradation of the one or more neuropeptide analogs and to minimize any adverse side effects in the subject. Pharmaceutically acceptable carriers, excipients and diluents suitable for therapeutic use are well known in the pharmaceutical art, and are described, for example, in Remington's Pharmaceutical Sciences, Maack Publishing Co. (A. R. Gennaro (Ed.) 1985).

Administration of analgesic compositions as described herein may be accomplished by any effective route, e.g., orally or parenterally. Methods of parenteral delivery include, for example, intra-arterial, subcutaneous, intramedullary, intravenous, intramuscular, intrasternal, intracavernous, intrathecal, intrameatal, intraurethral injection or infusion techniques, as well as intranasal, sublingual, buccal, rectal, and vaginal administration.

Analgesic compositions as described herein for oral administration can be formulated using pharmaceutically acceptable carriers well known in the art, in dosages suitable for oral administration. Such carriers enable the analgesic compositions to be formulated as tablets, pills, dragees, capsules, liquids, gels, syrups, slurries, suspensions, etc., suitable for ingestion by a subject.

Analgesic compositions for oral administration can be obtained, for example, through combination of one or more neuropeptide analog compounds with a solid excipient through, for instance, known granulation processes for providing compositions suitable for tableting or for inclusion in a capsule. In other embodiments, analgesic compositions for oral administration as described herein can be obtained, through combination of one or more neuropeptide analog compounds with a solid excipient, optionally grinding the resulting mixture, and processing the mixture of granules, after adding suitable additional compounds, if desired, to obtain tablets or dragee cores. Examples of excipients suitable for formulating analgesic compositions for oral administration include carbohydrate or protein fillers. Such excipients include, but are not limited to: sugars, including lactose, sucrose, mannitol, or sorbitol, starch from corn, wheat, rice, potato, or other plants; cellulose such as methyl cellulose, hydroxypropylmethyl-cellulose, or sodium carboxymethyl-cellulose, and gums including arabic and tragacanth, as well as proteins, such as gelatin and collagen. If desired, disintegrating or solubilizing agents may be added, such as the cross-linked polyvinyl pyrrolidone, agar, alginic acid, or a salt thereof, such as sodium alginate. Where pharmaceutical formulations of the analgesic compositions described herein are formulated using dragee cores, such cores may be provided with suitable coatings, such as concentrated sugar solutions, which may also contain, for example, gum arabic, talc, polyvinylpyrrolidone, carbopol gel, polyethylene glycol, and/or titanium dioxide, lacquer solutions, and suitable organic solvents or solvent mixtures.

In further embodiments, analgesic compositions suited for oral administration can be formulated, for example, as push-fit capsules made of gelatin, as well as soft, sealed capsules made of gelatin and a coating such as glycerol or sorbitol. Push-fit capsules can contain one or more analgesic compounds mixed with, for example, filler or binders such as lactose or starches, lubricants such as talc or magnesium stearate, and, optionally, stabilizers. In soft capsules, the one or more neuropeptide analogs may be dissolved or suspended in suitable liquids, such as fatty oils, liquid paraffin, or liquid polyethylene glycol with or without stabilizers.

Where the analgesic compositions are provided as pharmaceutical compositions or dosage forms for oral administration, such compositions may optionally include one or more pharmaceutically acceptable sweetening agents, preservatives, dyestuffs, flavorings, or any combination thereof. When the composition is in the form of a solid, unit dosage form, such as a tablet, the compositions may include a core formulation covered in one or more of a protective, functional or cosmetic coating, as is well known in the art. Moreover, in particular embodiments, dyestuffs or pigments may be added to a dosage form for oral administration or a coating included in or provided over such dosage form for purposes of product identification or to characterize the quantity of active compound (i.e., dosage).

In specific embodiments, analgesic compositions for parenteral administration include one or more MEGylated neuropeptide analog compounds. For injection, the analgesic compositions described herein may be formulated in aqueous solutions, preferably in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, where an analgesic composition is formulated as a suspension, the composition may also contain suitable stabilizers or agents, which increase the solubility of one or more neuropeptide analog compounds to allow for the preparation of highly concentrated formulations.

Analgesic compositions according to the present description may be manufactured according to techniques known in the art (e.g., by means of conventional mixing, dissolving, granulating, dragee-making, levigating, emulsifying, encapsulating, entrapping or lyophilizing processes). In particular embodiments, the analgesic compositions described herein may also be modified to provide appropriate release characteristics, e.g., sustained release or targeted release, by conventional means (e.g., through the use of a functional coating and/or known matrices or materials providing sustained or targeted release of active agents). After the analgesic compositions described herein have been prepared, they can be placed in an appropriate container and labeled for use.

Methods of treating pain and other neurological disorders are provided herein. In particular embodiments, the methods described herein comprising administering a therapeutically effective amount of an analgesic composition according to the present description to a subject in need thereof. In certain embodiments, the methods may further include the step of identifying a subject in pain, identifying a subject at risk of suffering pain or discomfort, or identifying a subject suffering from a disease or disorder that causes pain or discomfort, such as, for example, those described herein, followed by administering a therapeutically effective amount of an analgesic composition according to the present description.

The amount of an analgesic composition actually administered in a given method will be dependent upon the individual to which treatment is to be applied, the nature of the condition to be treated, and the amount of neuropeptide analog compound material included in the composition. The amount of analgesic composition administered may be an optimized amount, such that a desired therapeutic effect is achieved without an unacceptable level of side-effects. With the benefit of the teachings provided herein, determination of a therapeutically effective dose is well within the capability of those skilled in the art. Of course, the skilled person will realize that divided and partial doses are also within the scope of the methods described herein.

Therapeutic efficacy and possible toxicity of analgesic compositions described herein can be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index and can be expressed as the ratio $ED_{50}/LD_{50}$. Analgesic compositions which exhibit large therapeutic indices may be selected for administration to subjects. Data obtained from cell culture assays and animal studies may be used in formulating a range of dosages for use in an intended subject or class of subjects (e.g., humans). In particular embodiments, the amount of an analgesic composition administered to a subject provides a dose of the one or more neuropeptide analog compounds that result in a circulating concentration that lies within a range of circulating concentrations that include the $ED_{50}$, while exhibiting little or no toxicity. The dosage of a given neuropeptide analog compound may vary within this range, depending, for example, upon the dosage form employed, sensitivity of the subject, and the route of administration selected.

Methods for treating pain as described herein include methods of treating specific diseases and disorders that result in or are associated with discomfort or pain. For example, the methods described herein can be used to treat one or more diseases and disorders selected from chronic back pain, spinal cord injuries, peripheral nerve injuries, traumatic brain injuries, neurodegenerative disorders, fibromyalgia, postherpetic neuralgia, diabetic neuropathy, traumatic mononeuropathy, complex regional pain syndrome, adjuvant analgesic, rhizotomy/nerve ablation, preemptive analgesia/amputations, chemical exposure, chemotherapy-induced neuropathy, cancer, opioid withdrawal, and chronic neuropathic pain.

The methods and analgesic compositions disclosed herein can be used in combination with other compositions or treatment methods. As used herein, the phrase "in combination with" refers to a method by which at least one or more compositions in addition to the analgesic compositions as disclosed herein is administered to the subject. In certain embodiments, therefore, a method involving administration of a combination of compositions comprises, administering an analgesic composition as described herein in combination with at least one of the following: opioids and opioid peptides, morphine, hydroxymorphine, fentanyl, oxycodone, codeine, capsaicin, antiepileptic drugs (e.g., carbamazepine, primidone, gabapentin, pregabalin, diazepam, felbamate, fluorofelbamate, lamotrigine, lacosamide, levetiracetam, phenobarbital, phenyloin, fos-phenyloin, topiramate, valproate, vigabatrin, zonisamide, and oxcarbazepine), nonsteroidal anti-inflammatory drugs (NSAIDs), local anesthetics (e.g., lidocaine), glutamate receptor antagonists, NMDA antagonists, alpha-adrenoceptor agonists and antagonists, adenosine, cannabinoids, NK-1 antagonist (e.g., CI-021), antidepressants (e.g., amitriptyline, desipramine, imipramine), analogs and derivatives of galanin, somatostatin, neurotensin, neuropeptide Y, delta-sleep inducing peptide, enkephalins, oxytocin, cholecystikinin, calcitonin, cortistatin, nociceptin and other neuropeptide-based therapeutics. In another embodiment, the analgesic compositions as disclosed herein may be administered to the subject in combination with two or more additional compositions.

Throughout this application, various publications are referenced. The disclosures of these publications in their entireties are hereby incorporated by reference into this application in order to more fully describe the state of the art to which this invention pertains.

EXAMPLES

Example 1

Several MEGylated galanin analogs were chemically synthesized using solid-phase peptide synthesis protocols. In this example, two strategies were used to introduce MEGylated amino acids into a truncated galanin analog. One strategy was to replace a lipoamino acid with a MEGylated amino acid, as seen in Gal-BX shown in FIG. 1. Another strategy included replacing an amino acid with a MEGylated amino acid, as seen in Gal-B92 shown in FIG. 1. Table 1 summarizes structures of example galanin-based analogs that contain MEGylated amino acids that vary by the number of monodispersed polyethylene glycol (MPEG) repeats ranging from 4 to 24. As seen in Table 1, Sar is sarcosine, and N-Methyl-Trp is N-methyl-tryptophan.

Gal-58, Gal-93, Gal-103, and Gal-104 were synthesized with preloaded Fmoc-Lys (Boc)-Clear Rink Amide resin and Fmoc-Lys (Mmt)-OH was coupled to the peptide's second position. After coupling with all the remaining amino acids, an Mmt-group was removed by HAc/TFE/DCM (1:2:7), and then the resin was neutralized by 10% DIEA/DCM, different MPEG-acids were coupled to give the desired products.

Figure 2:
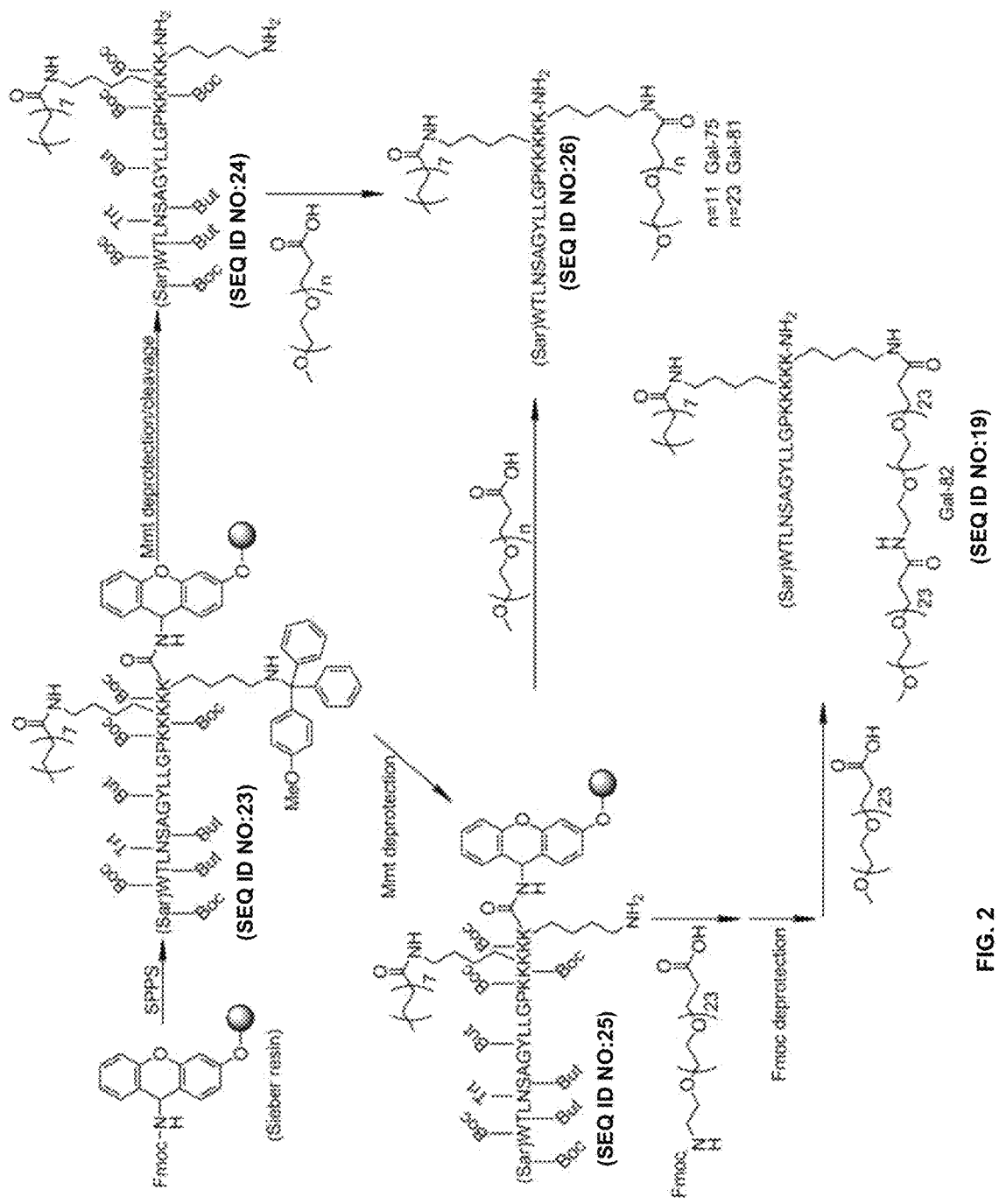
FIG. 2 shows one embodiment of the synthesis of neuropeptide analogs according to the present description.

The synthesis of Gal-75, Gal-78, Gal-81, Gal-82, and Gal-91 was accomplished from the same intermediate, as shown in FIG. 2. Weak acid liable TG Sieber resin was selected to conjugate PEG acid on C-terminal or in peptide chain.

Figure 3:
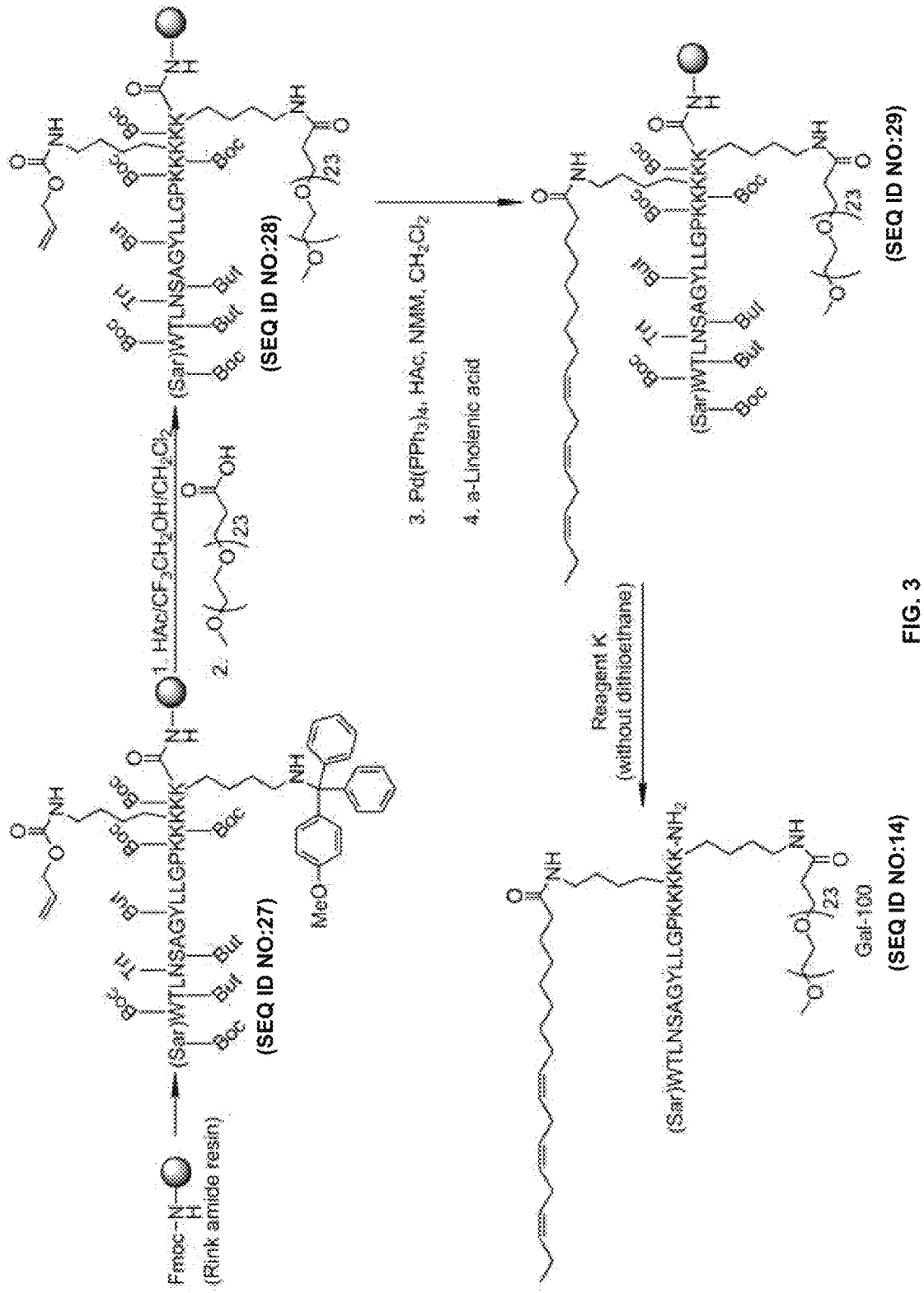
FIG. 3 shows another embodiment of the synthesis of neuropeptide analogs according to the present description.

The synthesis of Gal-100 and Gal-105 involved stepwise deprotection/conjugation methods as shown in FIG. 3. α-Linolenic acid is a light and air sensitive unsaturated fatty acid, so the conjugation of α-Linolenic acid was designed in the last step. Aloc/Mmt orthogonal protecting groups were selected to fulfill the modification of peptides with PEGylation and lipidization. Since alloc-deprotection uses acetic acid as scavenger, which will remove Mmt-simultaneously, Mmt needed to be removed firstly. So the side chain of C-terminal lysine was protected with Mmt-, the other Lysine at position 3 was protected with Aloc-. After the peptide was synthesized on resin, the Mmt-group was deprotected with HAc/TFE/DCM (1:2:7) and then PEGylated with $MPEG_{24}$-acid. Aloc was removed with Pd $(P(Ph_3))_4$/HAc/NMM/DCM and then α-Linolenic acid was conjugated to give the target product. In the cleavage of the unsaturated fatty acids modified peptide (such as α-Linolenyl), common cleavage reagents such as reagent K without dithioethane (TFA/Thioanisole/PhOH/$H_2O$) or TFA/TIPS/$H_2O$, all gave a large quantity of isomer, especially with long cleavage times,

TABLE 1

| Analog | Sequence |
| --- | --- |
| Gal-58 | (Sar)WTLNSAGYLLGPKK(Lys-$MPEG_4$)K-$NH_2$ (SEQ ID NO: 5) |
| Gal-103 | WTLNSAGYLLGPKK(Lys-$MPEG_4$)K-$NH_2$ (SEQ ID NO: 6) |
| Gal-104 | (N-Methyl-Trp)TLNSAGYLLGPKK(Lys-$MPEG_4$)K-$NH_2$ (SEQ ID NO: 7) |
| Gal-50 | (Sar)WTLNSAGYLLGPKK(Lys-$MPEG_{12}$)K-$NH_2$ (SEQ ID NO: 8) |
| Gal-75 | (Sar)WTLNSAGYLLGPKK(Lys-Pal)K(Lys-$MPEG_{12}$)-$NH_2$ (SEQ ID NO: 9) |
| Gal-93 | WTLNSAGYLLGPKKKK(Lys-$MPEG_{24}$)-$NH_2$ (SEQ ID NO: 20) |
| Gal-B92 | (Sar)WTLNSAGYLLGPKKKK(Lys-$MPEG_{24}$)-$NH_2$ (SEQ ID NO: 11) |
| Gal-81 | (Sar)WTLNSAGYLLGPKK(Lys-Pal)K(Lys-$MPEG_{24}$)-$NH_2$ (SEQ ID NO: 12) |
| Gal-91 | WTLNSAGYLLGPKK(Lys-Pal)K(Lys-$MPEG_{24}$)-$NH_2$ (SEQ ID NO: 13) |
| Gal-100 | (Sar)WTLNSAGYLLGPKK(Lys-α-Lnn)K(Lys-$MPEG_{24}$)-$NH_2$ (SEQ ID NO: 14) |
| Gal-105 | WTLNSAGYLLGPKK(Lys-α-Lnn)K(Lys-$MPEG_{24}$)-$NH_2$ (SEQ ID NO: 15) |
| Gal-82 | (Sar)WTLNSAGYLLGPKK(Lys-Pal)K(Lys-($MPEG_{24}$-NH-$PEG_{24}$))-$NH_2$ (SEQ ID NO: 19) | probably attributing to the double bound (cis/trans) isomers which can be induced at strong acid (TFA) conditions. This isomerization can be inhibited at low temperatures (0° C.), but the peptides are not fully deprotected at this condition. Therefore, room temperature was selected. Reagent K without dithioethane (TFA/Thioanisole/PhOH/H$_2$O 85/5/5/5) was used as the cleavage recipe, cleavage time was monitored with HPLC. The cleavage reaction was completed after 40 minutes, accompanied with 30% isomer.

The general synthetic procedures for the galanin analogs described herein are as follows: TG Sieber resin (0.19 meq) was purchased from Novabiochem. m-dPEG™-24 acid and N-Fmoc-Amido-dPEG™-24 acid were purchased from Quanta biodesign Limited. Fmoc-N-methyl-Trp (Boc)-OH was purchased from Bachem Inc. All other reagents were purchased from Chemimpex International Inc.

Reactions were performed under N$_2$ atmosphere, unless otherwise indicated. Automatic solid phase peptide synthesis (SPPS) was operated in a Symphony peptide synthesizer. Preparative HPLC was performed on a Waters 600 pump system equipped with a Waters 2487 dual wavelength detector (λ1) 220 nm, λ2) 280 nm) and a preparative Vydac diphenyl column (219TP101522). Analytical HPLC used an analytical Vydac diphenyl column (219TP54). The HPLC mobile phases are buffer A, 100% water (0.1% TFA), and buffer B, 90% acetonitrile (0.1% TFA). MALDI-TOF MS was conducted at the University of Utah Core Facility.

For the synthesis of Gal-58, 2-fold of Fmoc-Lys (Mmt)-OH was manually coupled to the preloaded Lys (Boc)-Rink Amide Clear resin by PyBop method. After coupling with all the remaining amino acids, 10 mL HAc/TFE/DCM (1:2:7) was added to the resin with shaking for 6 to 10 min to remove Mmt group. The deprotecting process was monitored to check for the solution to change color from yellow to clear. After neutralization with 10% DIEA/DCM, MPEG4-acid (MeO(OH$_2$OH$_2$O)$_4$OH$_2$COOH) was coupled to the resin using PyBop method. The peptide was cleaved with Reagent K (TFA-phenol-water-thioanisole-1,2-dithioethane 82.5:5:5:5:2.5), precipitated out from MTBE and purified with preparative HPLC (Vydac diphenyl column).

For Gal-93 and Gal-103, 2-fold of Boc-Trp (Boc)-OH was coupled instead of Fmoc-Trp (Boc)-OH in the peptides synthesis, following the same procedure as described in the synthesis of Gal-58.

For Gal-104, 2-fold of Fmoc-N-methyl-Trp (Boc)-OH was coupled manually for 24 h, and then Fmoc was removed with 20% piperidine/NMP, following the same procedure as Gal-58.

For Gal-91 and Gal-92, Fmoc-Lys (Mmt)-OH was coupled to Rink Amid clear resin, following by the same procedure as Gal-58.

For the general intermediate synthesis of Gal-75, Gal-78, Gal-81, and Gal-82, TG Sieber resin was selected for the flexible modification on N-Lysine of galanin analogues. Fmoc-based PyBop coupling protocols were used as previously described. 5-fold Fmoc-amino acids/PyBop/DIEA (1:1:2, molar ratio) were applied in peptide synthesis. Firstly, Fmoc-Lys (Mmt)-OH was coupled to Sieber resin, followed by the coupling of all the remaining Fmoc-protected amino acids. The N-terminal amino acid was coupled with Boc-capped Sarcosine to facilitate Lysine side chain modification for the synthesis of Gal-82, which uses Fmoc-protected PEG24 acid to synthesize the PEG48 moiety. Fmoc-Lys (Palmitoyl)-OH was coupled manually. After the coupling was finished, the Mmt-group of N-Lysine at the C-terminal end was removed by the reagents HAc/CF$_3$CH$_2$OH/OH$_2$Cl$_2$ (1:2:7) for 6×10 min. The resin was neutralized with 10% DIEA in OH$_2$Cl$_2$ for 5 min, and then washed with OH$_2$Cl$_2$ to give the general intermediate resin for the synthesis of Gal-75, Gal-78, Gal-81, and Gal-82.

Additionally, for Gal-81, 1.5-fold of m-dPEG™-24 acid/PyBop/HOBt/DIEA (1:0.98:1:2) was added to Mmt-deprotected resin with shaking for 24 h until ninhydrin test was negative. The peptide was cleaved from the resin with Reagent K (TFA-phenol-water-thioanisole-1,2-dithioethane 82.5:5:5:5:2.5) for 2 h. After evaporation of TFA, the residues were precipitated with MTBE and purified by RP-HPLC to give the PEGylated galanin analogue Gal-81. Gal-75 was made using the same method as described in Gal-81, however MPEG12-acid was coupled instead of m-dPEG™-24 acid. Alternative methods for the syntheses of Gal-75 and Gal-81 including removing Mmt and cleaving the protected intermediate from Sieber resin simultaneously with 1% TFA in 95% DCM/5% TES (triethylsilane) as indicated in FIG. 2; then conjugating the intermediate with dPEG-acids by PyBop method to get the final target peptides, after neutralized with 10% DIEA in DCM.

For Gal-82, 1.5-fold of N-Fmoc-Amido-dPEG™24 acid/PyBop/HOBt/DIEA (1:0.98:1:2) was added to Mmt-deprotected resin for 24 h, and then Fmoc was removed. m-dPEG™-24 acid/PyBop/HOBt/DIEA (1:0.98/1:2) was coupled to the resin, following the same cleavage and purification method as Gal-81 to give Gal-82.

For Gal-100, 2-fold of Fmoc-Lys (Mmt)-OH was coupled manually by PyBop method to Rink Amide Clear resin, followed with the coupling of Fmoc-Lys (Boc)-OH and Fmoc-Lys (Aloc)-OH. After all the remaining amino acids were coupled, HAc/TFE/DCM (1:2:7) was added to the resin to remove the Mmt group, and then the resin was neutralized with 10% DIEA/CH$_2$Cl$_2$, and m-dPEG™-24 acid was coupled using same method as disclosed for Gal-81. Aloc was deprotected with tetrakis(triphenylphosphine)palladium(0) (Pd(PPh$_3$)$_4$, 0.23 g, 0.2 mmol) in 2.78 mL DCM/AcOH/N-methylmorpholine (NMM) for 2 h. The resin was then washed with CH$_2$Cl$_2$, 0.5% DIEA/CH$_2$Cl$_2$ to remove AcOH, 0.02 M sodium diethyldithiocarbamate solution in NMP and to remove Palladium residues, CH$_2$Cl$_2$. α-Linolenic acid was coupled for 20 h. 5 ml TFA/PhOH/Thioanisole/H$_2$O (85/5/5/5) was added to the resin under N$_2$ and protected from light. After 40 min, TFA was evaporated in vacuum and MTBE was added to precipitate the products. The crude peptide was purified by preparative RP-HPLC to give the target peptide Gal-100. For Gal-105, the same synthetic method for Gal-100 was followed, only Boc-Trp (Boc)-OH was used at the N-terminal amino acid.

Example 2

Figure 4:
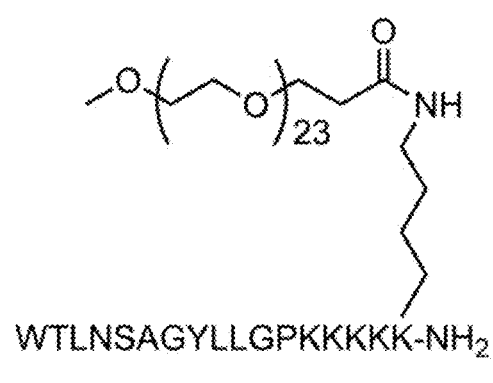
FIG. 4 shows the structure of the MEGylated galanin analog Gal-93, prepared according to the present description.

The galanin analog Gal-93 (SEQ ID NO: 20), as shown in FIG. 4, was tested in animal models for its effect on pain and epilepsy. As shown in Table 2, the biological testing of Gal-93 revealed that this analog had no apparent antiepileptic activity in the 6 Hz model of epilepsy; however it displayed analgesic activities in several pain models as disclosed herein. Under identical screening conditions, the lipoamino acid-containing compound, Gal-B2 (not shown), exhibited the anticonvulsant activity with 4/4 mice protected at time points 30 min, 60 min and 120 min (Bulaj et al, 2008, J Med Chem, vol 51, p. 8038-8047).

TABLE 2 # of protected mice from seizures (from groups of 4 mice), at a
dose 4 mg/kg of Gal-93, following intraperitoneal administration

| time   | 15 min | 30 min | 60 min | 120 min | 240 min |
|--------|--------|--------|--------|---------|---------|
| # mice | 0/4    | 0/4    | 0/4    | 0/4     | 0/4     |

Gal-93 and other MEGylated analogs were tested using the formalin test of acute and chronic hyperalgesia in mice. A summary of the results is presented in Table 3. The formalin test was performed according to the method described by Tjolsen et al. (Tjolsen A, Berge O G, Hunskaar S, Rosland J H, Hole K. The Formalin Test: An Evaluation of the Method. Pain 53(2), 237; 1992). More specifically, an injection of 0.5% formalin is made into the plantar region of the right hind paw of a mouse. This elicits a distinct behavioral profile in response to the formalin injection characterized by the mouse licking the affected paw. The behavior is characteristically biphasic in nature. For example, immediately following the injection the mouse intensely licks the paw for approximately 5-10 min. This initial behavior is considered phase 1 (acute) and is thought to be mediated primarily by chemical activation of local C-fibers. The acute phase is followed by a brief latent (usually <5 min) period where there is little or no behavioral activity. A more prolonged (about 20 to 30 min) period of licking then ensues which constitutes phase 2 of the response (inflammatory). Prior to the administration of the test drug or vehicle, each mouse undergoes a 15-min conditioning period in one of several 6" tall plexiglass cages (4" diameter) that are placed in front of a mirror. It is in these tubes that mice are observed for the licking activity for the duration of the experiment. Following conditioning, the test substance is dosed i.p. after which the mouse is returned to its home tube. At the TPE of the test substance, formalin is injected sub-dermally into the plantar surface of the right hind foot in a volume of 20 μl with a 27 gauge stainless steel needle attached to a Hamilton syringe. The bevel of the needle is placed facing down toward the skin surface.

Following the injection of the formalin, each mouse was observed for the first 2 min of 5-min epochs until 45 min had elapsed since the administration of the test drug. The cumulative length of licking for each 2-min time period was recorded. An animal receiving the requisite volume of vehicle was alternated with each mouse given the test peptide. Area under the curve (AUC) and subsequent percent of control for drug-treated animal groups (n=8) was determined using the GraphPad Prism Version 3.03. Total AUC was calculated for both the test substance and control groups for both the acute and inflammatory phases. The AUC for individual animals for each phase was also calculated and converted to percentage of total AUC of control. The average and S.E.M. for both the drug treated and control percentages were then calculated and tested for significant differences. The results showed that Gal-93 and Gal-81 significantly reduced the duration of licking, suggesting analgesic activity, in both the acute and inflammatory phases of the mouse formalin test. Gal-100, Gal-104 and Gal-105 significantly reduced the duration of licking, suggesting analgesic activity, in the inflammatory phase of the mouse formalin test.

TABLE 3

| Analog Name | Sequence | AUC Acute | AUC Inflammatory |
|-------------|----------|-----------|------------------|
| Gal-103 | WTLNSAGYLLGPKK(Lys-MPEG$_4$)K-NH$_2$ (SEQ ID NO: 6) | 66.3 ± 14.6 | 75.6 ± 8.9* |
| Gal-81  | (Sar)WTLNSAGYLLGPKK(Lys-palmitoyl)K(Lys-MPEG$_{24}$) (SEQ ID NO: 12) | 19.7 ± 7.2** | 2.9 ± 2.2** |
| Gal-93  | WTLNSAGYLLGPKKKK(Lys-MPEG$_{24}$) (SEQ ID NO: 20) | 34.9 ± 6.6** | 49.6 ± 3.5** |
| Gal-100 | (Sar)WTLNSAGYLLGPKK(Lys-α-Lnn)K(Lys-MPEG$_{24}$) (SEQ ID NO: 14) | 83.08 ± 13.34 | 33.78 ± 3.04** |
| Gal-105 | WTLNSAGYLLGPKK(Lys-α-Lnn)K(Lys-MPEG$_{24}$) (SEQ ID NO: 15) | 108.3 ± 24.8 | 69.9 ± 6** |

*$P < 0.05$,
**$P < 0.01$ compared with vehicle treated control mice

Table 4 summarizes a dose-response study of the analgesic activity of Gal-93 in the rat formalin assay following intravenous administration into the femoral vein of the rats. Prior to the administration of formalin, each rat underwent a 30-min conditioning period in one of several 30.5 cm tall plexiglass tubes (15 cm diameter). Prior to placement in the plexiglass tubes, a metal band was fitted on to the right hind leg and secured with a drop of superglue as such, animals acclimate to both the tube and the metal band. It is in these plexiglass cylinders that rats were later observed for the flinching behavior that accompanies hind-paw formalin injection. Following a 30 min conditioning period, 50 μl of 2.5% formalin was injected sub-dermally into the plantar surface of the right hind foot in a volume of 50 μl using a 27 gauge stainless steel needle attached to a Hamilton syringe. The bevel of the needle was placed facing down toward the skin surface. Following the injection of the formalin each animal was placed in a new plexiglass cylinder on top of a detection unit, and the Automated Nociception Analyzer (Dept. of Anesthesiology, Univ. California, San Diego) is initiated. The number of flinches was collected for every minute for the duration of the 60 minute experiment. In these studies Gal-93 was administered i.v. at 5 mg/kg and formalin was injected into the paw at 10 min, 30 min or 60 min following Gal-93 administration. The number of flinches recorded over the 60 min following formalin injected was calculated as area-under-the-curve (AUC) as described for the mouse formalin assay. These studies showed a peak activity for Gal-93 at 60 min following i.v. administration in the rat formalin test.

TABLE 4

| Dose i.v. & Time of formalin administration post-treatment | Acute Phase AUC | Inflammatory Phase AUC | Number of Rats |
|---|---|---|---|
| 5 mg/kg, 10 min | 64.5 ± 17.9 | 91.3 ± 6.5 | 2 |
| 5 mg/kg, 30 min | 68.4 ± 8.6 | 70.8 ± 19.8 | 4 |
| 5 mg/kg, 60 min | 34.3 ± 5.1 | 55.8 ± 11.0 | 2 |

Example 3

An acetic acid induced abdominal constriction (writhing) assay was used to test the analgesic effect of neuropeptide analogs. In this assay of chemical nociception, a 0.6% acetic acid solution is injected into the peritoneal cavity of adult male CF-1 mice where it directly activates nociceptors and produces inflammation of both the visceral (subdiaphragmatic) and subcutaneous (muscle wall) tissues. This results in a characteristic "writhing response" in the mouse involving lengthwise stretching of the torso and concave arching of the back and extensions of the hind-limbs (Jensen T S, Yaksh T L. Effects of an intrathecal dopamine agonist, apomorphine, on thermal and chemical evoked noxious responses in rats. Brain Res. 1984 Apr. 2; 296(2):285-93). The writhing behaviors were observed while the mice were kept in 6" tall plexiglass cages (4" diameter).

Following a 15 minute conditioning period, the test neuropeptide analog compound was administered intraperitoneally (i.p.) and the mouse returned to its home tube. One hour after injection of the test neuropeptide analog compound, the acetic acid solution (0.6% v/v) is injected i.p. at a volume of 0.1 ml/10 g body weight using a 1 ml syringe with a 26G ⅜ bevel needle. Following the injection of the acetic acid, the total number of abdominal constrictions was recorded over a 30 minute observation period. An animal receiving an equivalent volume of vehicle was observed side by side with the animal receiving the test compound. One writhe is considered to have occurred with the adoption of the typical posture and to have terminated upon resumption of a normal posture. The average number of abdominal constrictions was compared between groups using the Student's t-test comparison.

Figure 5:
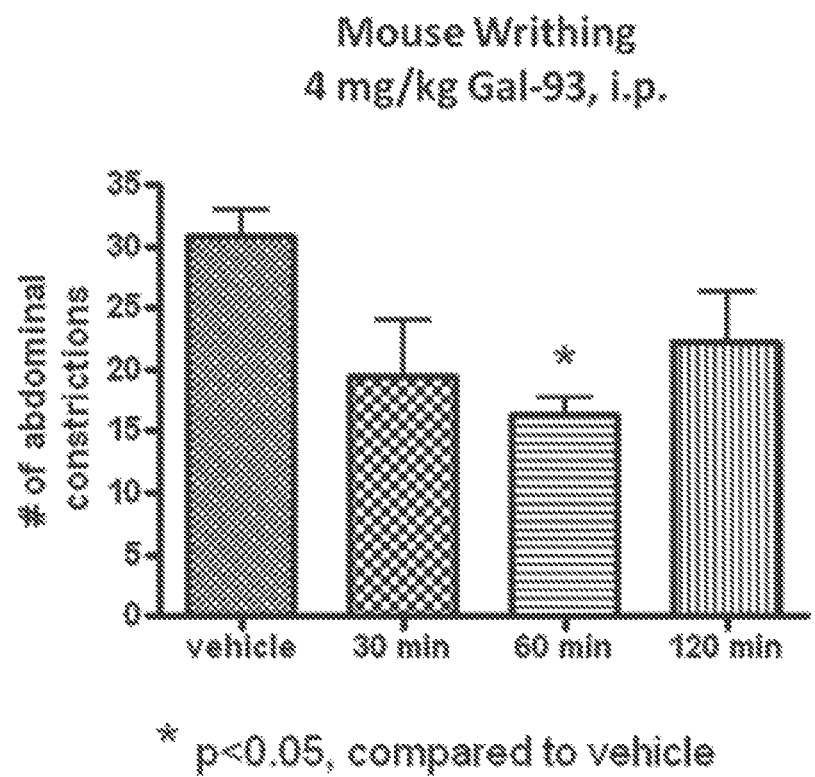
FIG. 5 is graph showing the analgesic activity of the galanin analog Gal-93 demonstrated by the mouse abdominal constriction assay.
Figure 6:
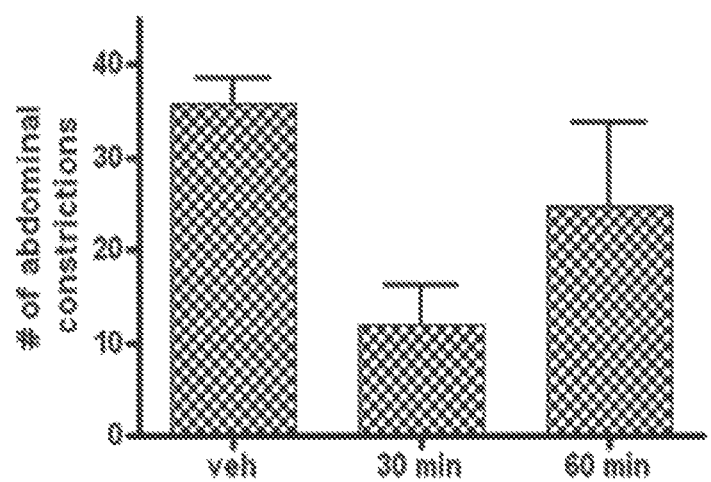
FIG. 6 is graph showing the analgesic activity of the neuropeptide Y analog NPY-B42 demonstrated by the mouse abdominal constriction assay.

As shown in FIGS. 5 and 6, Gal-93 (SEQ ID NO: 20) and NPY-B42 (SEQ ID NO: 21) reduced the number of abdominal constrictions, as compared to vehicle alone, with a peak effect post i.p. administration (4 mg/kg, n=3-4 per group) of 60 minutes and 30 minutes, respectively.

Example 4

The rat partial sciatic nerve ligation was used as a model of neuropathic pain. Briefly, a small incision is made unilaterally in the upper thigh of anesthetized rats and approximately ⅓ to ½ of the sciatic nerve is tied off by passing a "taper by 130-4" needle attached to size 8 nylon sutures through the nerve. This ligation is performed dorsal to where the sciatic nerve bifurcates and only a portion of the sciatic nerve is tied off to maintain some motor response. After a 7 day recovery period, the rats are tested for the development of consistent, mechanical allodynia (pain response to a non-noxious stimulus). The animals are each put in a bottomless plexiglass box placed on a ¼" wire mesh (stainless steel or galvanized) platform. After at least a 30-min conditioning period, a baseline mechanical sensitivity is determined. This procedure is done by applying a series of calibrated Von Frey fibers perpendicularly to the plantar surface of each hind paw in between the pads or further back toward the heel. The 50% threshold for foot withdrawal is determined by using the step procedure. That is, after a positive response (withdrawal of the foot) is noted a weaker fiber is applied. If there is no recoil the next highest/stiffer/thicker fiber is again applied and so forth. This is repeated for 5 steps.

Following the determination of the initial baseline sensitivity the rats were given an i.p. injection of the neuropeptide analog test compound and the mechanical threshold was assessed at 1, 2, 4, 6, and 24 hrs post-injection to determine the duration of action of the test compound and its time of peak effect. The withdrawal threshold for each animal at each time point was computed using the "xoxox" procedure (Chaplan S R, Bach F W, Pogrel J W, Chung J M, Yaksh T L. Quantitative assessment of tactile allodynia in the rat paw. J Neurosci Methods. 1994 53(1):55-63). The average and S.E.M. of the pre-drug withdrawal threshold were calculated and compared to the average withdrawal threshold of the group at each time point following drug treatment. The average and S.E.M. for both the drug treated and control percentages were calculated and tested for significant difference.

Figure 7:
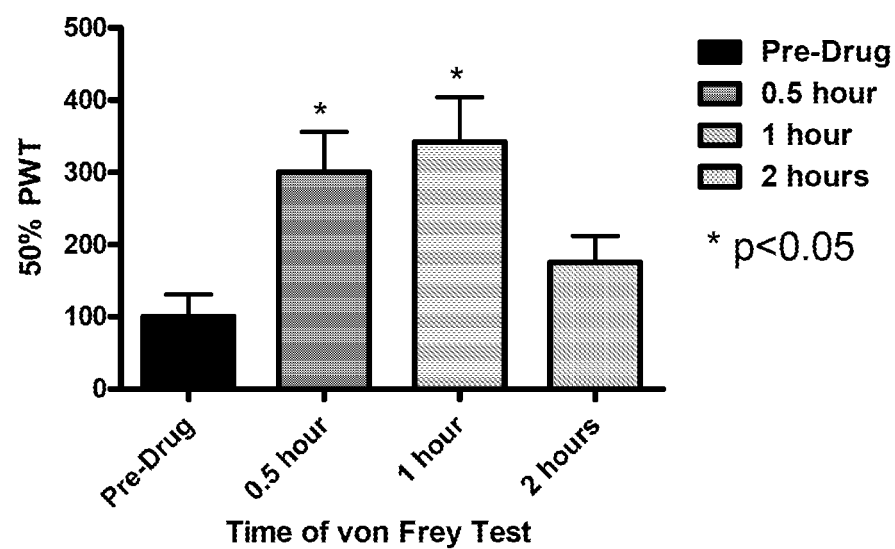
FIG. 7 is a graph showing the analgesic activity of the galanin analog Gal-93 demonstrated by the rat partial sciatic nerve ligation assay.
Figure 8:
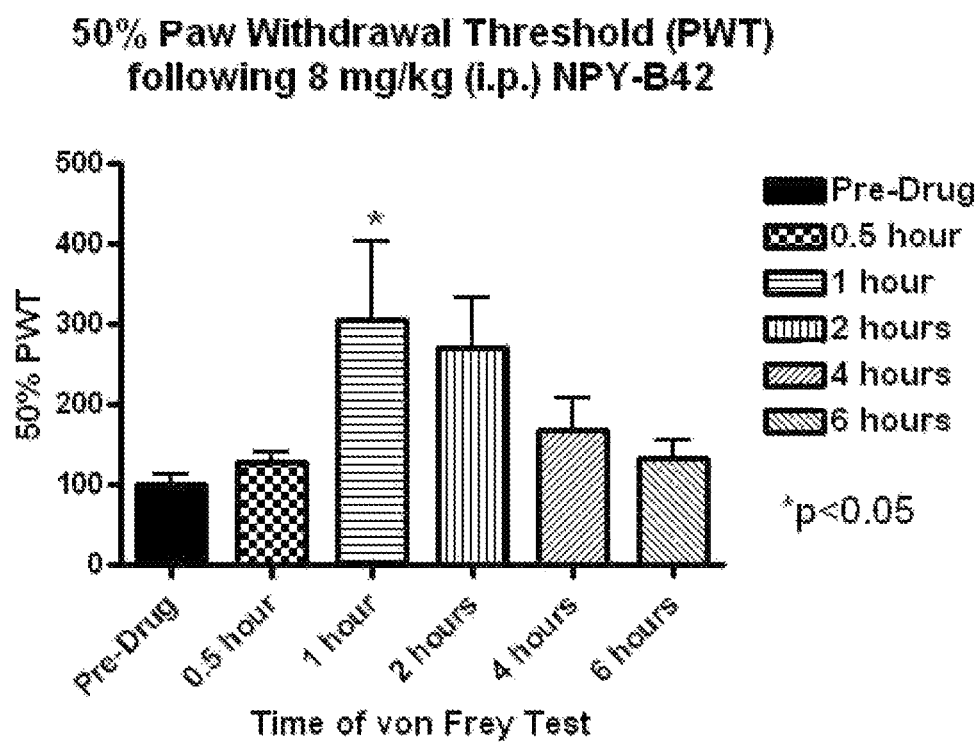
FIG. 8 is a graph displaying the analgesic activity of the neuropeptide Y analog NPY-B42 demonstrated by the rat partial sciatic nerve ligation assay.

As shown in FIG. 7, the mice treated with the galanin analog Gal-93 had a higher 50% paw withdrawal threshold (PWT) when compared to the pre-drug untreated controls, with peak activity at 1 hr post i.p. administration of Gal-93 (2 mg/kg, n=4 per group). As shown in FIG. 8, mice treated with NPY-B42 (SEQ ID NO: 21) had a higher 50% PWT when compared to the pre-drug untreated controls, with peak activity at 2 hr post i.p. administration of NPY-B42 (8 mg/kg, n=8 per group).

Example 5

The mouse carrageenan assay was used as a model of chemically induced inflammatory pain. For this model, male CF-1 mice weighing 25-35 g were injected with 25 ul of carrageenan (2% in 0.9% NaCl, lambda carrageenan) into the plantar surface of the right hind paw. Latency to paw withdrawal was tested 3 h following carrageenan administration. Briefly, mice are placed on a glass surface heated to 30° C. Radiant heat is applied to the plantar surface of the paw, through the glass plate, until a withdrawal of the paw from the glass surface occurs (Ding et al. 1997, Hargreaves et al. 1988). Latency to paw withdrawal is measured from the onset of heat application until a full paw withdrawal occurs. Two measurements are taken from each paw (injected and non-injected), with at least 1 min between measurements, which are then averaged. The mean withdrawal latency from the non-injected paw is subtracted from the carrageenan-injected paw to obtain a withdrawal latency difference for each animal. Experimental conditions, including animal habituation, glass plate temperature, and thermal stimulus intensity have been optimized such that withdrawal latency differences for carrageenan-injected/vehicle-treated animals are approximately 4 s.

Experimental neuropeptide analog compounds were dissolved in 1% Tween20/0.9% NaCl and administered via intraperitoneal injection at varying doses 1 h (Gal-93) or 2 h (NPY-B42) prior to withdrawal latency testing. The neuropeptide analog compounds were considered to have full analgesic efficacy when the withdrawal latency difference was zero. All data are presented as means±standard error.

Comparisons between two means were performed using a Student's t-test. Comparisons between multiple means were performed using a one- or two-way ANOVA followed by a Newman-Keuls or Bonferroni test, respectively.

Figure 9:
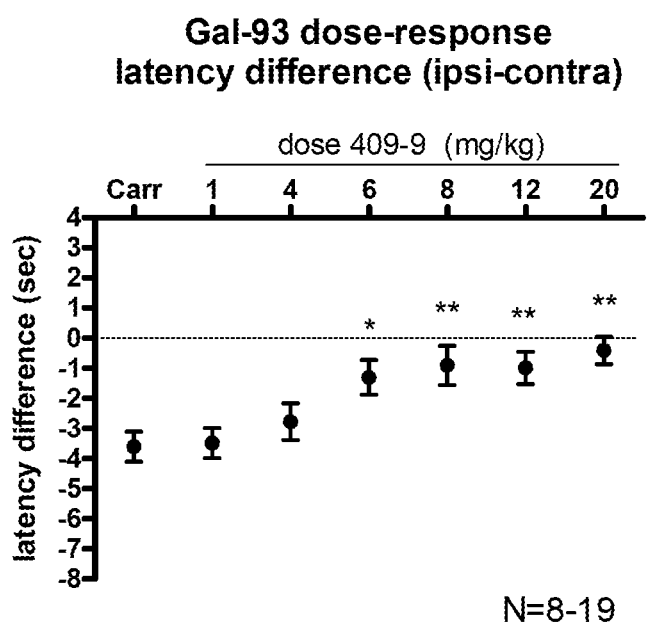
FIG. 9 displays the results of the mouse carrageenan assay using the neuropeptide analog Gal-93.
Figure 10:
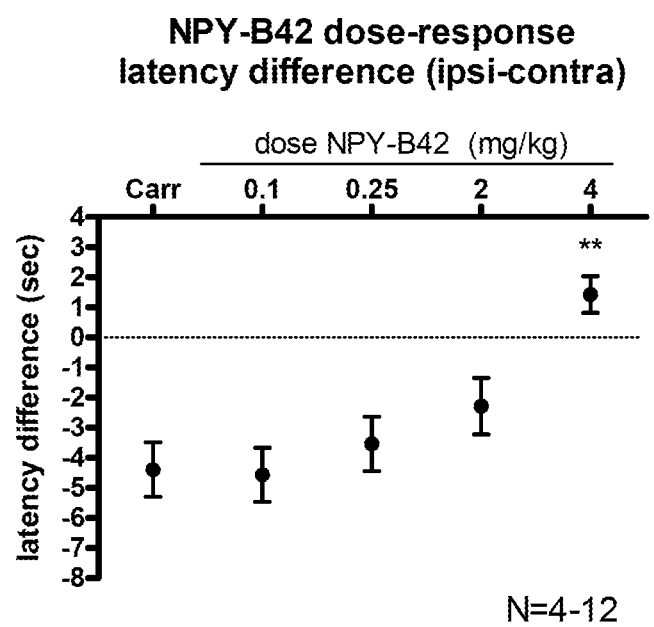
FIG. 10 displays the results of the mouse carrageenan assay using the neuropeptide analog NPY-B42.

As shown in FIG. 9, the galanin analog Gal-93 increased the withdrawal latency difference when compared to the carrageenan controls. The 6 mg/kg and higher doses of Gal-93 tested showed significant reversal of the carrageenan induced hyperalgesia relative to the controls. As shown in FIG. 10, the NPY-B42 analog increased the withdrawal latency when compared to the carrageenan controls. The 4 mg/kg dose of NPY-B42 showed significant reversal of the carrageenan induced hyperalgesia relative to the controls.

Example 6

In this example, the cardiovascular effects of neuropeptide analog compounds were assessed following i.v. administration in rats. Male Sprague-Dawley rats weighing between 250 and 350 g were anesthetized and implanted with femoral vein and artery catheters. On the following day, the arterial catheter was connected to a pulse pressure transducer for continuous monitoring of blood pressure (BP) and heart rate (HR). The venous catheter is connected to a remote syringe for intravenous (iv) infusions. The galanin analog compound Gal-93 was dissolved in 1% Tween 20/0.9% NaCl and administered over approximately 1 min (0.25 mg/kg iv, 1 ml infusion volume). Mean BP/HR samples were taken at baseline, dosing, and at 1, 5, 10, 20, 30, 40, 50, and 60 minutes after dosing. Prior to dosing and 60 min after dosing, baroreceptor reflex sensitivity was assessed by infusion of phenylephrine (9 ug, 0.05 ml infusion volume), which elicits a BP increase of 40-60 mmHg and a corresponding bradycardia of 50-150 beats/min (in vehicle-treated animals). In addition, blood samples were collected from the arterial catheter at baseline, 30 min, and 60 min after dosing for the determination of hematocrit, plasma protein, and blood glucose. Body temperature was also monitored, with samples taken at baseline, 15 min, 30 min, and 60 min after dosing. Mean BP and HR were obtained from 30-60 s digitized pulse pressure recording segments at the previously mentioned time points. For determination of baroreceptor reflex sensitivity, BP and HR were obtained at the highest and lowest points, respectively, following phenylephrine infusion.

The results of the cardiovascular safety evaluation of Gal-93 and NPY-B42 (n=3 rats) are shown in Table 5. All data are presented as means±standard error. For blood pressure (BP) and heart rate (HR) the maximal change observed during the time-points (1-60 minutes) is recorded. Comparisons between the two means were performed using a Student's t-test. Comparisons between multiple means were performed using a one- or two-way ANOVA followed by a Newman-Keuls or Bonferroni test, respectively. In these studies, neither Gal-93 or NPY-B42 showed statistically significant difference from vehicle treated rats with any of the cardiovascular parameters measured.

Example 7

Metabolic stability assay: Peptide stability was assessed in a rat serum assay. One mL of 25% rat serum was incubated at 37° C. for 10 min, prior to addition of the analogs. Reactions were prepared by adding each analog, dissolved in nanopure $H_2O$, to a solution containing 25% rat blood serum and 0.1 M Tris-HCl, pH 7.5 to a final peptide concentration of 20 μM. At appropriate time intervals (ranging up to 8 h), 200 μL aliquots were withdrawn and added to 100 μL "quenching solution" (15% trichloroacetic acid in 40% isopropanol). Isopropanol (40%, aqueous solution) was added to quenching mixture (this step improved recovery of the Gal-B2 and other analogs). Upon precipitation with the quenching mixture, the samples were incubated at −20° C. for 15 min and centrifuged at 12,000 rpm. The supernatant was analyzed using HPLC separation with an YMC ODS-A™ 5 μm 120 Å column (Waters, Cat#: AA12S052503WT). In cases where analog peaks overlapped with peaks observed in the "serum-only" control samples, the gradient was optimized by changing the composition of the mobile phases, column temperature or HPLC column (for example $C_8$ rather than diphenyl column). Recovery of the analogs was assessed by spiking "serum-only" control samples after the trichloroacetic acid precipitation with known amounts of the analog. Metabolic stability was assessed by monitoring the disappearance of the analogs over a period of 8 h. This was accomplished by comparison the area under the curve for the peak corresponding to the intact analog at each time point. Half-time, $t_{1/2}$, for each analog was calculated using the average of three independent experiments for each time point. Results were plotted on a log-scale plot using the Kaleidagraph software. Linear curve-fit analysis was used to fit the time-course of the degradation of the analogs according to the following formula: $t_{1/2}$ (h)=(Ln(50)−b)/(m), where "m" represents the slope of the line and "b" is the y-intercept.

It will be obvious to those having skill in the art that many changes may be made to the details of the above-described embodiments without departing from the underlying principles of the invention. The scope of the present invention should, therefore, be determined only by the following claims.

TABLE 5

| NAX# | BP min | HR max | BP max | HR min | glucose 30 min | glucose 60 min | HCT 30 min | HCT 60 min | plasma protein 30 min | plasma protein 60 min | temperature 30 min | temperature 60 min |
|---|---|---|---|---|---|---|---|---|---|---|---|---|
| | | | | | Phenylephrine post-treatment response | | | | | | | |
| Vehicle | 111 ± 5 | 427 ± 10 | 158 ± 3 | 334 ± 8 | 81 ± 16 | 83 ± 13 | 40 ± 2 | 43 ± 3 | 6.4 ± 0.2 | 7.1 ± 0.2 | 37.6 ± 0.2 | 37.5 ± 0.1 |
| Gal-93 | 113 ± 3 | 455 ± 39 | 164 ± 7 | 268 ± 20 | 70 ± 16 | 61 ± 11 | 43 ± 2 | 37 ± 3 | 7.5 ± 0.1 | 6.8 ± 0.4 | 37.6 ± 0.2 | 37.2 ± 0.3 |
| NPY-B42 | 108 ± 5 | 451 ± 14 | 161 ± 4 | 291 ± 26 | 78 ± 5 | 73 ± 4 | 42 ± 2 | 42 ± 1 | 6.5 ± 0.4 | 6.8 ± 0.3 | 37.2 ± 0.2 | 36.9 ± 0.4 |

The invention claimed is:

1. A method of treating pain in a subject, the method comprising:
   administering to the subject a pharmaceutically effective amount of a compound comprising a galanin analog that does not have measurable activity in the central nervous system;
   wherein the galanin analog comprises a truncated galanin comprising at least one lysine residue covalently attached to a monodisperse oligoethylene glycol unit, wherein the galanin analog is selected from at least one of SEQ ID NO: 8, 9, 10, 11, 12, 13, 14, 15, 16, 19, and 20.

2. A method of treating pain in a subject, the method comprising administering to the subject a pharmaceutically effective amount of a neuropeptide analog, wherein the neuropeptide analog is set forth in SEQ ID NO: 20.

* * * * *